(12) United States Patent
Poznansky et al.

(10) Patent No.: US 7,951,364 B2
(45) Date of Patent: May 31, 2011

(54) CAR RECEPTOR AS A MEDIATOR OF MIGRATORY CELL CHEMOTAXIS AND/OR CHEMOKINESIS

(75) Inventors: Mark C. Poznansky, Charlestown, MA (US); Edward M. Brown, Milton, MA (US); David T. Scadden, Weston, MA (US); Ivona T. Olszak, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 820 days.

(21) Appl. No.: 11/429,902

(22) Filed: May 8, 2006

(65) Prior Publication Data

US 2006/0292689 A1 Dec. 28, 2006

Related U.S. Application Data

(60) Division of application No. 10/002,854, filed on Nov. 1, 2001, now Pat. No. 7,176,243, which is a continuation-in-part of application No. PCT/US00/15440, filed on Jun. 2, 2000.

(60) Provisional application No. 60/200,861, filed on May 1, 2000.

(51) Int. Cl.
*A01N 63/00* (2006.01)
(52) U.S. Cl. ............ 424/93.7; 424/93.71; 435/366
(58) Field of Classification Search .................. None
See application file for complete search history.

(56) References Cited

U.S. PATENT DOCUMENTS

| 5,686,574 A | 11/1997 | Moore et al. |
|---|---|---|
| 5,756,448 A | 5/1998 | Moore et al. |
| 5,766,951 A * | 6/1998 | Brown .................. 435/407 |
| 5,879,875 A * | 3/1999 | Wiggins et al. ............ 435/1.1 |
| 5,981,599 A | 11/1999 | Moe et al. |
| 6,184,254 B1 | 2/2001 | Bukoski et al. |
| 6,224,860 B1 * | 5/2001 | Brown .................. 424/93.7 |
| 6,277,557 B1 * | 8/2001 | Burger et al. ................ 435/2 |
| 7,176,243 B2 * | 2/2007 | Poznansky et al. ........ 514/649 |

FOREIGN PATENT DOCUMENTS

| EP | 0256989 | 2/1988 |
|---|---|---|
| EP | 0852144 | 7/1998 |
| WO | WO 01/83546 | 11/2001 |

OTHER PUBLICATIONS

Adams et al., "Bone mineral contributes to Bone Marrow Hematopoiesis through the calcium sensing receptor." *American Society for Hematology*, 2001 Annual Meeting, Orlando, FL, Dec. 7-11, 2001. Abstract Only.
Aida et al. *Biochem. Biophys. Res. Commun.* Sep. 14, 1995; 214(2):524-9 Abstract only.
Brundage et al. *Science* Nov. 1, 1991;254(5032):703-6 Abstract Only.
Burger et al. *Blood* Dec. 1, 1999;94(11):3658-67. Abstract Only.
Catapano, *Eur Heart J* Jan. 1997; 18 Suppl A: A80-6. Abstract Only.
Chattopadhyay et al., *Brain Res Mol Brain Res* Aug. 15, 2001;92(1-2):172-6. Abstract Only.
Elferink, et al., *Chem Biol Interact* Mar. 30, 1995;95(1-2):203-4. Abstract Only.
Elferink et al., *Biochem Biophys Res Commun.* 1992, 182(2):864-9. Abstract Only.
Ferrari, et al., *Dev Biol* Sep. 5, 1999;213(2):269-82. Abstract Only.
Ganju, et al., *J Biol Chem* Sep. 4, 1998;273(36):23169-75.
Genbank Accession D50855 Human mRNA for Ca-sensing receptor, complete cds. Jun. 23, 1999.
Gerszten, et al., *Nature* Apr. 22, 1999;398(6729):718-23, Abstract Only.
Guinamard, et al. *J Exp Med* May 3, 1999;189(9):1461-6. Abstract Only.
Henry, *Clin Invest Med* Nov. 1987;10(6):601-5. Abstract Only.
Herbette et al., *Blood Press Suppl* 1998;2:10-7. Abstract Only.
House, et al., *J Bone Miner Res* Dec. 1997; 12(12) :1959-70.
Huang, et al., *J Leukoc Idol* May 1997; 61(5):624-9 Abstract Only.
Jordan, et al., *J Clin Invest* Oct. 1999; 104(8):1061-9.
Kim, et al., *J Clin Invest* Dec. 1999; 104(12):1751-9.
Laster, et al. *J Immunol* Jul. 1, 1988, 141(I):221-7 Abstract Only.
Liu, et al.,*J Immunol* Nov. 15, 1999;163(10):5649-55. Abstract Only.
Marasco, et al., *Am J Pathol* Mar. 1980;98(3):749-68. Abstract Only.
Marks, et al., *J Cell Biol* Jan. 1990; 110(1):43-52.
Marra,., et al , *Hepatology*. 999 Jan;29( ): 40-8. Abstract Only.
McColl, et al., *J Immunol* Sep. 1, 1999;163(5):2829-35 Abstract Only.
Meshulam, et al., *J Immunol*. Sep. 15, 1986;137(6):1954-60.
Mishima, et al., *Clin Exp Metastasis* Aug. 1998; 16(6):541-50. Abstract Only.
Murdoch, et al., *Cytokine* Sep. 1999;11(9):704-12. Abstract Only.
Murdoch, et al., *Immunology* Sep. 1999;98(1):36-41. Abstract On y.
Nayler., *J Cardiovasc Pharmacol* 999;33 Suppl 2:S7-11. Abstract Only.

(Continued)

*Primary Examiner* — Leon B Lankford
(74) *Attorney, Agent, or Firm* — Edwards Angell Palmer & Dodge LLP; Peter C. Lauro, Esq.; Melissa Hunter-Ensor, Esq.

(57) ABSTRACT

This invention relates to methods and compositions for modulating movement of eukaryotic cells with migratory capacity. More specifically, the invention relates to methods and compositions for modulating movement of CaR receptor expressing cells of hematopoietic, neural, epithelial, endothelial, or mesenchymal origin, in a specific site in a subject. The foregoing are useful, inter alia, in the treatment of conditions characterized by a need to modulate migratory-cell movement associated with specific sites in a subject. Specific sites include sites of inflammation and modulation of migratory-cell movement is movement away from an agent source, or repulsion. The invention also relates to methods for manipulating hematopoeitic progenitor cells and related products. In particular the invention includes methods and products for using CaR receptor-related compositions to enhance mobilization of hematopoietic progenitor cells, to improve the efficiency of targeting cells to the bone marrow, and/or to modulate hematopoietic progenitor cell function.

10 Claims, 6 Drawing Sheets

OTHER PUBLICATIONS

Nikol, et al., *Eur Heart J* 997 Jan; 8 Suppl A:A105-9. Abstract Only.
Olszak, et al , *J Clin Invest* May 2000; 105(9):1299-1305.
Paoletti, et al , *Am J Cardiol* Nov. 20, 1990;66(18):28H-31H. Abstract Only.
Paoletti, et al., *Ann N Y Acad Sci* 988;522:390-8. Abstract Only.
Paoletti, et al., *J Cardiovasc Pharmacol* 1995;25 Suppl 3:S6-10. Abstract Only.
Raicu, et al., *J Submicrosc Cytol Pathol* 1997 Jut;29(3):317-28 Abstract Only.
Riviere et al., *Blood* Mar. 1, 1999;93(5):1511-23, Abstract Only.
Schmitz et al. *Atherosclerosis* 1991 88(2-3): 109-32.
Schwartz *Fundam Clin Pharmacol* 1988 2(2): 103-20.
Schweizer, et al., *J Leukoc Biol* Mar. 1996;59(3):347-56.
Shi, et al., *FASEB J* Mar. 1996; 10(4):491-501.
Sperling, et al., *J Clin Invest* Feb. 1993;91(2):651-60. Abstract Only.
Sugimoto, et al., *J Bone Miner Res* Dec. 1993;8(12):1445-52. Abstract Only.
Suzuki, et al., *Int Immunol* May 1997;9(5):763-9. Abstract Only.
Tulenko, et al., *Int J Cardiol* Dec. 31, 1997;62 Suppl 2:S55-66, Abstract Only.
Weinstein, et al., *Am J Cardiol* Jan. 30, 1987;59(3):163B-172B. Abstract Only.
Yamaguchi, et al., *Endocrinology* 1998 Attg;139(8):3561-8. Abstract Only.
Yamaguchi et al. *Journal of Bone and Mineral Research* 1998 13, 10.
Yamaguchi, et a ., *J Bone Miner Res* Sep. 1998;13(9):1390-7. Abstract Only.
Yamaguchi., et al., *Adv Pharmacol* 2000;47:209-53.
Young., et al., *Blood* Oct. 1999 ;94(7):2533-6. Abstract Only.
Zou., *Zhonghua Yi Xue Za Zhi* Jul. 1992;72(7):424-6, 447 Abstract Only.

* cited by examiner

CAR RECEPTOR AS A MEDIATOR OF MIGRATORY CELL CHEMOTAXIS AND/OR CHEMOKINESIS

RELATED APPLICATIONS

This application is a Divisional application of U.S. application Ser. No. 10/002,854, filed on Nov. 1, 2001 now U.S. Pat. No. 7,176,243, which is a continuation-in part of International application Ser. No. PCT/US00/15440 filed on Jun. 2, 2000, entitled the CaR RECEPTOR AS A MEDIATOR OF MIGRATORY CELL CHEMOTAXIS AND/OR CHEMOKINESIS, designating the United States and published in English as International Publication Number WO 01/83546 on Nov. 8, 2001, from which priority under 35 U.S.C. §365(c) is claimed and which claims the benefit of U.S. provisional patent application Ser. No. 60/200,861, filed on May 1, 2000. The contents of each of these applications are hereby expressly incorporated by reference.

GOVERNMENT SUPPORT

The work leading to the instant invention was funded in part by grants HL-44851, DK-50234, DK-41415, DK-48330, and DK-52005, from the National Institutes of Health. Accordingly, the United States Government may have certain rights to this invention.

FIELD OF THE INVENTION

This invention relates to methods and compositions for modulating movement of eukaryotic cells with migratory capacity. More specifically, the invention relates to methods and compositions for modulating movement of CaR receptor expressing cells of hematopoietic, neural, epithelial, endothelial, or mesenchymal origin, in a specific site in a subject. The foregoing are useful, inter alia, in the treatment of conditions characterized by a need to modulate migratory-cell movement associated with specific sites in a subject. Specific sites include sites of inflammation and modulation of migratory-cell movement is movement away from an agent source, or repulsion. The invention also relates to methods for manipulating hematopoeitic progenitor cells and related products. In particular the invention includes methods and products for using CaR receptor-related compositions to enhance mobilization of hematopoietic progenitor cells, to improve the efficiency of targeting cells to the bone marrow, and/or to modulate hematopoietic progenitor cell function.

BACKGROUND OF THE INVENTION

Cell movement in response to specific stimuli is observed to occur in prokaryotes and eukaryotes (Doetsch R N and Seymour W F, *Life Sciences*, 1970, 9:1029-1037; Bailey G B et al., *J Protozool*, 1985, 32:341-346). Cell movement seen in these organisms has been classified into three types; chemotaxis or the movement of cells along a gradient towards an increasing concentration of a chemical; negative chemotaxis which has been defined as the movement down a gradient of a chemical stimulus and chemokinesis or the increased random movement of cells induced by a chemical agent. The receptors and signal transduction pathways for the actions of specific chemotactically active compounds have been extensively defined in prokaryotic cells. Study of *E. Coli* chemotaxis has revealed that a chemical which attracts the bacteria at some concentrations and conditions may also act as a negative chemotactic chemical or chemorepellent at others (Tsang N et al., *Science*, 1973, 181:60-69; Repaske D and Adler J., *J Bacteriol*, 1981, 145:1196-1208; Tisa L S and Adler J., *Proc Natl Aca Sci U.S.A.*, 1995, 92:10777-10781; Taylor B L and Johnson M S., *FEBS Lett*, 1998, 425:377-381).

Accumulation of immune cells at sites of injury or infection is a critical dimension of host defense that is achieved by highly conserved mediators of cell adhesion and cell motility. The large family of protein cytokines capable of inducing cell migration is termed collectively, chemokines, which can be produced by virtually every cell type in mammals (Wells, T. N., et al., *Trends Pharmacol Sci*, 1998, 19:376-380; Baggiolini, M., Nature, 1998, 392:565-568; Luster, A. D., *N Engl J Med*, 1998, 338:436-445). Chemokines mediate their function via seven-transmembrane, G protein-coupled receptors (7-TMR); the absence of either chemokines or their receptors results in marked phenotypic alterations in mice (Luster, A. D., supra; Ma, Q., et al., *Proc Natl Acad Sci USA*, 1998, 95:9448-53; Ma, Q., et al., *Immunity*, 1999, 10:463-471). These include altered inflammatory responses to pathogenic or allergenic challenges and mitigated atherosclerotic changes in models of vascular disease (Ross, R., *N Engl J Med*, 1999, 340:115-26). Extracellular fluids at sites of injury or infection have been reported to contain high concentrations of calcium (Menkin, V., *Biochemical mechanisms in inflammation*, 1981, Charles Thomas Publisher, Illinois, USA; Lin, C-Y and Huang, T-P., *Nephron*, 1991, 59:90-95; Kaslick, R. S., et al., *J Periodonto*, 1970, 41:93-7), and chronic inflammatory conditions and atherosclerosis are associated with deposition of calcium salts (Ross, R., supra; Tanimura, A., et al., *J Exp Pathol*, 1986, 2:261-73; McCarty, D. J., *Dis Mon*, 1994, 40:253-299). The concentration of calcium in such settings can be substantially higher than that of the serum (Menkin, V., supra; Lin, C-Y and Huang, T-P., supra; Kaslick, R. S., et al., supra). We hypothesized that such extracellular calcium gradients actively participate in modulating the immune response, acting via the CaR.

The calcium-sensing receptor (CaR) is a member of the 7-TMR superfamily and is responsive to $Ca^{++}$ concentrations within the millimolar range found in extracellular fluids (Brown, E. M., et al., Nature, 1993, 366:575-80) (SEQ ID NOs 1 and 2). It was originally defined by its role in mediating systemic calcium homeostasis; however, it has been subsequently shown to have pleiotropic effects including altering cellular proliferation, differentiation and apoptosis (Brown, E. M., et al., *Vitamins and Hormones*, 1999, 55:1-71; Lin, K. I., et al., *Biochem Biophys Res Commun*, 1998, 249:325-31; Freichel, M., et al., *Endocrinology*, 1996, 137:3842-8; McNeil, S. E., et al., *J Biol Chem*, 1998, 273:1114-20). In hematopoietic cells, it is expressed on mature monocyte/macrophages and subsets of progenitor populations in the bone marrow (House, M. G., et al., *J Bone Min Res*, 1997, 12:1959-1970; Yamaguchi, T., et al., *Biochem Biophys Res Commun*, 1998, 246:501-6). Animals engineered to be deficient in this receptor appear normal at birth, but die with severely elevated blood calcium levels within the first few weeks of life (Ho, C., et al., *Nat Genet* 1995, 11:389-94; Dutour, A., *Eur J Endocrinol*, 1996, 134: 542-3). Activation of the receptor is maximal at 5 mM $Ca^{++}$ (Brown, E. M., et al., *Vitamins and Hormones*, 1999, 55:1-71), and selective CaR activators have been developed that efficiently mimic $Ca^+$-induced activation through an allosteric mechanism (e.g., NPS R-467 and its less active stereoisomer, S-467) (Nemeth, E. F., et al., *Proc Natl Acad Sci USA*, 1998, 95:4040-5). These agents are low molecular weight compounds, termed "calcimimetics", that interact with the CaR's transmembrane domains and potentiate the actions of polycationic agonists, such as $Ca^{++}$ itself, which bind to the receptor's amino-terminal extracellular domain. Calcimimetics are currently in clinical trials for treating primary hyperparathyroidism, a disorder in which the CaR is underactive, and represent useful pharmacological tools for assessing the CaR's mediatory role in CaR-expressing cells in which high $Ca^{++}$ modulates cellular function. CaR signal transduction is mediated via a pertussis toxin (PTX)-inhibitable $G\alpha_i$ pathway as well as a PTX-insensitive mechanism, likely involving $G\alpha_{q/11}$ (Chen, C. J., et al., *Endocrinology*, 1989, 124:233-9; Varrault, A., et al., *Endocrinology*, 1995, 136:4390-6; Dare, E., et al., *J Mol Endocrinol*, 1998, 21:7-17).

SUMMARY OF THE INVENTION

Applicants have discovered that the CaR receptor plays an important role in chemotaxis and chemokinesis (collectively "migration") of eukaryotic cells. We describe herein compositions and methods relating to the migration of CaR receptor expressing cells. Pharmaceutical compositions containing the CaR receptor related agents, and various therapeutic and diagnostic methods utilizing the foregoing CaR receptor related agents, are also described in more detail below. The foregoing can be used, inter alia, in the treatment of conditions characterized by a need to modulate migratory-cell movement in specific sites in a subject. Important such sites include inflammation sites.

Applicants have also discovered novel ways for manipulating hematopoietic progenitor cells. Hematopoietic progenitor cells undergo a development stage-specific translocation during ontogeny and ultimately reside in the adult bone marrow. Maintenance of this highly regenerative cell pool through adult life is dependent upon their relative quiescence. It has been discovered, according to the invention, that the CaR receptor is involved in the regulation of hematopoietic progenitor cell properties such as quiescence and localization.

According to one aspect of the invention, a method of enhancing migration of CaR receptor expressing cells to a specific site in a subject is provided. The method involves, locally administering to a specific site in a subject in need of such treatment a $nonCa^{++}$ CaR receptor agonist in an amount effective to enhance migration of CaR receptor expressing cells to the specific site in the subject. The CaR receptor expressing cells can be hematopoietic cells, immune cells (including antigen presenting cells), neural cells, epithelial cells, endothelial cells (including endothelial cell progenitors), and/or mesenchymal cells. In certain embodiments, the CaR receptor expressing hematopoietic cells are hematopoietic progenitor cells. In some embodiments, the $nonCa^{++}$ CaR receptor agonist can be NPS R-467 and/or NPS S-467.

According to another aspect of the invention, a method of inhibiting migration of CaR receptor expressing cells to a specific site in a subject is provided. The method involves locally administering to a specific site in a subject in need of such treatment a CaR receptor antagonist, in an amount effective to inhibit migration of CaR receptor expressing cells to the specific site in the subject. In certain embodiments, the specific site is a site of inflammation. In other embodiments, when the specific site is the site of inflammation, the method further comprises co-administering an agent that is not a CaR receptor antagonist that inhibits migration of immune cells to the site of inflammation in the subject. In certain embodiments, the agent includes an anti-inflammatory agent and/or an immunosuppressant.

In certain embodiments, the subject has an autoimmune disease. In preferred embodiments, the autoimmune disease includes rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, systemic lupus erythematosus. In further embodiments, the subject has multiple sclerosis, an abscess, a transplant, an implant, atherosclerosis, and/or myocarditis. Preferred CaR receptor expressing cells are as described above. In certain embodiments, the CaR receptor antagonist is NPS-2143.

According to another aspect of the invention, a method of repelling CaR receptor expressing cells from a material surface is provided. The method involves coating a material surface with an amount of a CaR receptor antagonist effective to repel CaR receptor expressing cells from the material surface. In certain embodiments, the material surface is part of an implant. The material comprising the implant may be synthetic material or organic tissue material. Important CaR receptor antagonist, cell-types, and so on, are as described above.

According to another aspect of the invention, a method of attracting CaR receptor expressing cells to a material surface is provided. The method involves coating a material surface with a $nonCa^{++}$ CaR receptor agonist in an effective amount to attract CaR receptor expressing cells to the material surface. Important $nonCa^{++}$ CaR receptor agonists, cell-types, material surfaces and so on, are as described above.

According to a further aspect of the invention, a method of enhancing an immune response in a subject having a condition that involves a specific site is provided. The method involves locally administering to the specific site in a subject in need of such treatment a $nonCa^{++}$ CaR receptor agonist, in an amount effective to enhance immune cell migration to the specific site in the subject. In some embodiments, the specific site is a site of a pathogenic infection. In certain embodiments, the specific site is a germ cell-containing site. In further embodiments, the specific site is an area immediately surrounding a tumor.

According to yet another aspect of the invention, a method for enhancing migration of a cell toward a chemokine is provided. The method involves contacting a cell known to migrate toward a chemokine that is not a CaR receptor agonist with the chemokine and a CaR receptor agonist in a combined amount effective to enhance migration of the cell toward the chemokine, wherein the amount of CaR receptor agonist is effective to potentiate the amount of chemokine versus the same amount of the chemokine if administered without the CaR receptor agonist. Important CaR receptor agonists (including $Ca^{++}$), cell-types, and so on, are as described above. In certain embodiments, the chemokine is selected from the group consisting of MCP-1, MIP-1β, and SDF-1.

According to another aspect of the invention, a method for enhancing expression of a chemokine receptor in a cell is provided. The method involves contacting a cell expressing a chemokine receptor with a CaR receptor agonist in an effective amount to enhance expression of the chemokine receptor in the cell. Important CaR receptor agonists (including Ca++), cell-types, and so on, are as described above. In certain embodiments, the chemokine receptor is selected from the group consisting of CCR-2, CCR-5, and CXCR-4.

According to another aspect of the invention, a method for enhancing bone marrow engraftment following bone marrow transplantation is provided. The method involves contacting isolated bone marrow cells to be transplanted with a CaR receptor agonist in an effective amount to increase chemokine receptor expression in the isolated bone marrow cells to enhance bone marrow engraftment following bone marrow transplantation of said cells. Important CaR receptor agonists (including $Ca^{++}$), chemokine receptors, and so on, are as described above. If $Ca^{++}$ is used as the CaR receptor agonist, the $Ca^{++}$ concentration used to increase chemokine receptor expression in the isolated bone marrow cells is higher than the $Ca^{++}$ concentration found in the media in which the isolated bone marrow cells are kept/cultured. In certain embodiments, the isolated bone marrow cells are hematopoietic progenitor cells.

According to a further aspect of the invention, a method for enhancing bone marrow engraftment following bone marrow transplantation, is provided. The method involves contacting isolated bone marrow cells to be transplanted with an agent that increases CaR receptor expression in an effective amount to increase CaR receptor expression in the isolated bone marrow cells to enhance bone marrow engraftment following bone marrow transplantation of said cells. In some embodiments, the agent that increases CaR receptor expression is selected from the group consisting of $Ca^{++}$, Vitamin D, a chemokine, a CaR receptor agonist, and a CaR receptor nucleic acid. A preferred chemokine is the cytokine IL-1β. Important CaR receptor agonists (including $Ca^{++}$), chemokine receptors, and so on, are as described above. If $Ca^{++}$ is used as the CaR receptor agonist, the $Ca^{++}$ concentration used to increase chemokine receptor expression in the isolated bone marrow cells is higher than the $Ca^{++}$ concentration found in the media in which the isolated bone marrow cells are kept/cultured. In certain embodiments, the isolated bone marrow cells are hematopoietic progenitor cells.

A method for modulating hematopoietic progenitor cell function, is provided according to another aspect of the invention. The method involves contacting a hematopoietic progenitor cell with an agent that modulates CaR receptor expression in an effective amount to modulate CaR receptor expression in the hematopoietic progenitor cell to modulate its function. In important embodiments, the agent that modulates CaR receptor expression is selected from the group consisting of $Ca^{++}$, Vitamin D, a chemokine, a CaR receptor agonist, a CA receptor antagonist, a CaR receptor antisense agent, and a CaR receptor nucleic acid (see, e.g., SEQ ID NO:1).

According to another aspect of the invention, a method for inducing hematopoietic progenitor cell quiescence, is provided. The method involves contacting a hematopoietic progenitor cell with an agent that increases CaR receptor expression in an effective amount to increase CaR receptor expression in the hematopoietic progenitor cell to induce quiescence of the hematopoietic progenitor cell. The contacting may occur in vivo or in vitro.

In another aspect the invention provides a method for inhibiting hematopoietic progenitor cell-death. The method involves inducing hematopoietic progenitor cell quiescence according to any of the foregoing aspects and embodiments to inhibit hematopoietic progenitor cell-death. In important embodiments the hematopoietic progenitor cell is under environmental stress. Environmental stresses include increased temperatures (e.g., fever), physical trauma, oxidative, osmotic and chemical stress (e.g. a chemotherapeutic agent), and UV irradiation.

According to a further aspect of the invention, a method for inducing hematopoietic progenitor cell differentiation, is provided. The method involves contacting a hematopoietic progenitor cell with an agent that decreases CaR receptor expression in an effective amount to decrease CaR receptor expression in the hematopoietic progenitor cell to induce differentiation of the hematopoietic progenitor cell. In important embodiments, the agent that decreases CaR receptor expression is selected from the group consisting of a CaR receptor antagonist, and a CaR receptor antisense agent. In certain embodiments, the CaR receptor antagonist is NPS-2143. The contacting may occur in vivo or in vitro.

According to still another aspect of the invention, a method for enhancing mobilization of hematopoietic cells in a subject is provided. The method involves administering to a subject in need of such treatment a CaR receptor antagonist in an amount effective to enhance mobilization of hematopoietic cells in the subject. In certain embodiments, the CaR receptor antagonist is NPS-2143. In some embodiments, the hematopoietic cells are hematopoietic progenitor cells. In important embodiments, the hematopoietic cells are hematopoietic stem cells. In one embodiment, the subject is a bone marrow donor.

According to a further aspect of the invention, a method for treating a subject to enhance immune reactivity to a specific antigen in the subject, is provided. The method involves administering to a subject in need of such treatment an amount of a CaR receptor agonist together with an amount of a specific antigen, wherein the amount of the CaR receptor agonist is sufficient to enhance in the subject immune reactivity to the specific antigen versus the same amount of the specific antigen if administered without the a CaR receptor agonist. Important CaR receptor agonists (including $Ca^{++}$) are as described above. In certain embodiments, the method further comprises co-administering a non-CaR receptor agonist adjuvant. In important embodiments, the non-CaR receptor agonist adjuvant is Freund's incomplete adjuvant.

According to another aspect of the invention, a method for treating a subject to enhance immune tolerance in the subject, is provided. The method involves administering to a subject in need of such treatment an amount of a CaR receptor antagonist, wherein the amount of the CaR receptor antagonist is sufficient to enhance in the subject immune tolerance to a self or a non-self antigen. Important CaR receptor antagonists are as described above. In certain embodiments, the subject has an autoimmune disease. In preferred embodiments, the autoimmune disease includes rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, systemic lupus erythematosus. In further embodiments, the subject has multiple sclerosis, an abscess, a transplant, an implant, atherosclerosis, and/or myocarditis.

According to another aspect of the invention, a pharmaceutical preparation is provided. The pharmaceutical preparation comprises a CaR receptor related agent of the invention (CaR receptor agonist or CaR receptor antagonist) in an effective amount to modulate migration of a CaR receptor expressing cell, and a pharmaceutically acceptable carrier. Important CaR receptor related agents, cell-types, and so on, are as described above.

These and other aspects of the invention, as well as various advantages and utilities, will be more apparent with reference to the detailed description of the preferred embodiments.

BRIEF DESCRIPTION OF THE SEQUENCES

SEQ ID NO:1 is the nucleotide sequence of the human $Ca^{++}$-sensing Receptor (CaR) cDNA (GenBank Acc. No. D50855).
SEQ ID NO:2 is the predicted amino acid sequence of the translation product of the human $Ca^{++}$-sensing Receptor (CaR) cDNA (SEQ ID NO:1); (GenBank Acc. No. BAA09453.1).

BRIEF DESCRIPTION OF THE DRAWINGS

FIG. 2: Various bar graphs showing that monocytes migrate toward Ca$^{++}$ in a dose dependent manner that is inhibitable by pretreatment with PTX, genistein or herbimycin and is potentiated by the selective CaR activator, NPS R-467, and the chemokine, MCP-1.

DETAILED DESCRIPTION OF THE INVENTION

Figure 1A:
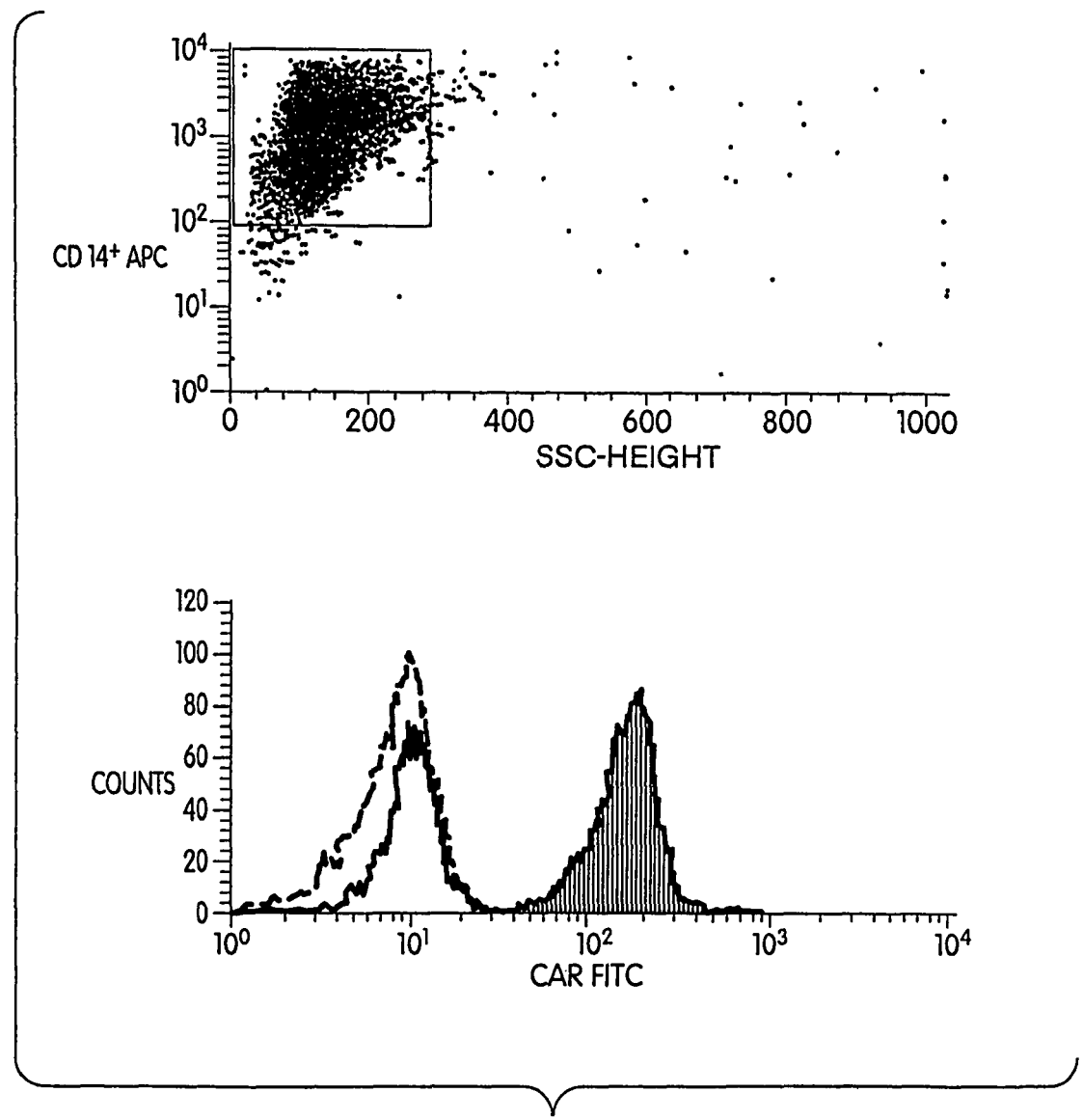
FIG. 1(a): Scattergram showing CaR positive stain on CD14$^+$ monocytes (upper panel), and inhibition of anti-CaR antibody binding to CaR by preincubating CD14$^+$ monocytes with CaR peptide (lower panel)

The invention involves the discovery that the CaR receptor plays an important role in chemotaxis and chemokinesis of cells. Pharmaceutical compositions containing the foregoing CaR receptor related agents, and various therapeutic and diagnostic methods utilizing the foregoing of CaR receptor related agents, are also described in more detail below. The foregoing can be used, inter alia, in the treatment of conditions characterized by a need to modulate migratory-cell movement in specific sites in a subject. Important such sites include inflammation sites.

"CaR receptor," as used herein, refers to a polypeptide (SEQ ID NO:2) encoded by the nucleic acid having a nucleotide sequence as set forth in anyone of GenBank Acc. Nos.: D50855 (SEQ ID NO:1) or NM_000388, or having a nucleic acid sequence as described in WO9418959, all of which are exressly incorporated herein by reference.

"CaR receptor related agents," as used herein, refer to molecules that can mimic (agonists) or block (antagonists) an effect of extracellular Ca$^{++}$ through the CaR receptor (described above), on a cell expressing such a receptor. The effect is chemotactic and/or chemokinetic (collectively "migratory") in nature. Exemplary such CaR receptor related agents include CaR receptor agonists, for example, Ca$^{++}$, CaR peptide (NPS Pharmaceuticals, Inc., Salt Lake City, Utah), NPS R-467 (NPS Pharmaceuticals), NPS S-467 (NPS Pharmaceuticals), and CaR receptor antagonists, for example NPS-2143 (NPS Pharmaceuticals), agonist binding agents as described below, and the molecules described in U.S. Pat. Nos. 5,858,684, 5,763, 569, and 5,688,938.

The invention, therefore, embraces binding agents which, for example, can be antibodies or fragments of antibodies having the ability to selectively bind to, for example, CaR receptor agonists and inhibit the migratory properties of the CaR receptor agonist (as described above). In important embodiments, the binding agents are antibodies. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

As used herein, a subject is a human, non-human primate, cow, horse, pig, sheep, goat, dog, cat or rodent. In all embodiments, human subjects and cells are preferred.

The chemotactic, chemokinetic (collectively "migratory") activity of the foregoing CaR receptor related agents on the different cell-types of the invention, can be detected using any of the transmigration systems described herein (see Examples), or a variety of other systems well known in the art (see, e.g., U.S. Pat. No. 5,514,555, entitled: "Assays and therapeutic methods based on lymphocyte chemoattractants," issued May 7, 1996, to Springer, T A, et al.).

According to one aspect of the invention, methods for modulating (either enhancing or inhibiting) migration of CaR receptor expressing cells to a specific site in a subject are provided. "CaR receptor expressing cells," as used herein, are cells that express the CaR receptor. Expression can be detected using techniques well known to those of ordinary skill in the art and include nucleic acid hybridization (e.g., Southern, Northern), PCR (Polymerase Chain Reaction), and immunohistochemistry.

The CaR receptor expressing cells can be, inter alia, hematopoietic cells, immune cells (including antigen presenting cells), neural cells, epithelial cells, endothelial cells (including endothelial cell progenitors), and/or mesenchymal cells. In certain embodiments, the CaR receptor expressing hematopoietic cells are hematopoietic progenitor cells.

"Hematopoietic cells" and/or cells of "hematopoietic origin" include, but are not limited to, pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. The hematopoietic cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the "hematopoietic origin" cells may be derived from in vitro cultures of any of the foregoing cells, and in particular in vitro cultures of progenitor cells.

"Hematopoietic progenitor cells" as used herein refer to immature blood cells having the capacity to self-renew and to differentiate into the more mature blood cells (also described herein as "progeny") comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). It is known in the art that such cells may or may not include $CD34^+$ cells. $CD34^+$ cells are immature cells present in the "blood products" described below, express the CD34 cell surface marker, and are believed to include a subpopulation of cells with the "progenitor cell" properties defined above. It is well known in the art that hematopoietic progenitor cells include pluripotent stem cells, multipotent progenitor cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage.

The hematopoietic progenitor cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for $CD34^+$ cells. As mentioned earlier, $CD34^+$ cells are thought in the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

"Immune cells," as used herein, refer to cells of hematopoietic origin (see above) that are involved in the specific recognition of antigens. Immune cells also include antigen presenting cells (APCs), such as dendritic cells or macrophages, B cells, T cells, etc.

Cells of neural origin ("neural cells"), include neurons and glia, and/or cells of both central and peripheral nervous tissue that express RR/B (see, U.S. Pat. No. 5,863,744, entitled: "Neural cell protein marker RR/B and DNA encoding same," issued Jan. 26, 1999, to Avraham, et al.).

Cells of epithelial origin ("epithelial cells"), include cells of a tissue that covers and lines the free surfaces of the body. Such epithelial tissue includes cells of the skin and sensory organs, as well as the specialized cells lining the blood vessels, gastrointestinal tract, air passages, ducts of the kidneys and endocrine organs.

Cells of mesenchymal origin ("mesenchymal cells"), include cells that express typical fibroblast markers such as collagen, vimentin and fibronectin.

Cells of endothelial origin are cells of the vasculature that are involved in blood vessel (formation (angiogenesis).

An embryonic stem cell is a cell that can give rise to cells of all lineages; it also has the capacity to self-renew.

A germ cell is a cell specialised to produce haploid gametes. It is a cell further differentiated than a stem cell, that can still give rise to more differentiated germ-line cells.

The invention in another part relates to the unexpected discovery that the CaR receptor related agents of the invention (and in particular CaR receptor agonists), enhance migration of a cell toward a chemokine. The method involves contacting a cell known to migrate toward a chemokine that is not a CaR receptor agonist with the chemokine and a CaR receptor agonist in a combined amount effective to enhance migration of the cell toward the chemokine, wherein the amount of CaR receptor agonist is effective to potentiate the amount of chemokine versus the same amount of the chemokine if administered without the CaR receptor agonist.

"Chemokines," as used herein, refer to a large family of protein cytokines capable of inducing cell migration. "Cytokine" is a generic term for nonantibody soluble proteins which are released from one cell subpopulation and which act as intercellular mediators, for example, in the generation or regulation of an immune response. See *Human Cytokines: Handbook for Basic & Clinical Research* (Aggrawal, et al. eds., Blackwell Scientific, Boston, Mass. 1991) (which is hereby incorporated by reference in its entirety for all purposes). Cytokines include, e.g., interleukins IL-1 through IL-15, tumor necrosis factors α & β, interferons α, β, and γ, tumor growth factor beta (TGF-β), colony stimulating factor (CSF) and granulocyte monocyte colony stimulating factor (GM-CSF). The action of each cytokine on its target cell is mediated through binding to a cell surface receptor. Cytokines share many properties of hormones, but are distinct from classical hormones in that in vivo, they generally act locally on neighboring cells within a tissue. The activities of cytokines range from promoting cell growth (e.g., IL-2, IL-4, and IL-7), and arresting growth (IL-10, tumor necrosis factor and TGF-β), to inducing viral resistance (IFN α, β, and γ). See Fundamental Immunology (Paul ed., Raven Press, 2nd ed. 1989); Encyclopedia of Immunology, (Roitt ed., Academic Press 1992) (which are hereby incorporated by reference in their entirety for all purposes). In certain embodiments, the cytokine is a cytokine with chemoattractant and/or chemokinetic properties. Examples of such cytokines include: PAF, N-formylated peptides, C5a, LTB$_4$, LXA4, chemokines: CXC, IL-8, GCP-2, GROα, GROβ, GROγ, ENA-78, NAP-2, IP-10, MIG, I-TAC, SDF-1α, BCA-1, PF4, Bolekine, MIP-1α, MIP-1β, RANTES, HCC-1, MCP-1, MCP-2, MCP-3, MCP-4, MCP-5 (mouse only), Leukotactin-1 (HCC-2, MIP-5), Eotaxin, Eotaxin-2 (MPIF2), Eotaxin-3 (TSC), MDC, TARC, SLC (Exodus-2, 6CKine), MIP-3a (LARC, Exodus-1), ELC (MIP-3β), I-309, DC-CK1 (PARC, AMAC-1), TECK, CTAK, MPIF1 (MIP-3), MIP-5 (HCC-2), HCC-4 CC-4), MIP-1γ (mouse only), C-10 (mouse only); C: Lymphotactin; CX$_3$C: Fracktelkine (Neurotactin). Most preferably, the cytokine is a member of the Cys-X-Cys family of chemokines (chemokines that bind to the CXCR-4 receptor). Preferred such agents of the invention include SDF-1α, SDF-1β, and met-SDF-1β. In further preferred embodiments, such fugetactic agents include other CXCR-4 receptor ligands. CXCR-4 ligands include, but are not limited to, HIV-1$_{IIIB}$ gp120, small molecules T134 and MD3100, and/or T22 ([Tyr5,12,Lys7]-polyphemusin II) (Heveker et al., Curr Biol, 1998, 8:369-76).

According to another aspect, the invention involves a method of repelling or attracting immune cells from and to a material surface. "Material surfaces" as used herein, include, but are not limited to, dental and orthopedic prosthetic implants, artificial valves, and organic implantable tissue such as a stent, allogeneic and/or xenogeneic tissue, organ and/or vasculature.

Implantable prosthetic devices have been used in the surgical repair or replacement of internal tissue for many years. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic and dental implants, use high performance metals such as cobalt-chrome and titanium alloy to achieve high strength. These materials are readily fabricated into the complex shapes typical of these devices using mature metal working techniques including casting and machining.

The material surface is coated or impregnated with an amount of a CaR receptor related agent (a CaR receptor agonist or CaR receptor antagonist) effective to modulate the migration of CaR receptor expressing cells (e.g., immune cells) toward or away from the coated material surface. In important embodiments, the material surface is part of an implant. In important embodiments, in addition to a CaR receptor related agent, the material surface may also be coated with a cell-growth potentiating agent, an anti-infective agent, and/or an antiinflammatory agent. Coatings or materials which can be impregnated are well known in the art. Some of the same materials used to make microspheres and the like, described below, may be used. Such materials are natural or synthetic, and may be polymers, gels, hydrogels, proteins, peptides, and the like.

A cell-growth potentiating agent as used herein is an agent which stimulates growth of a cell and includes growth factors such as PDGF, EGF, FGF, TGF, NGF, CNTF, and GDNF.

An anti-infective agent as used herein is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erytliromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebrainycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopaflngin; Sisomicin; Sisomicin Sulfate; Sparfioxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Antiinflammatory agents are as described below.

According to another aspect of the invention, a method of inhibiting migration of CaR receptor expressing cells to a specific site in a subject is provided. The method involves locally administering to a specific site in a subject in need of such treatment a CaR receptor antagonist, in an amount effective to inhibit migration of CaR receptor expressing cells to the specific site in the subject.

In one important embodiment, the invention provides a method of inhibiting migration of immune cells to a site of inflammation in the subject. "Inflammation" as used herein, is a localised protective response elicited by a foreign (non-self) antigen, and/or by an injury or destruction of tissue(s), which serves to destroy, dilute or sequester the foreign antigen, the injurious agent, and/or the injured tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products that are mediators of inflammatory responses (neutrophils, eosinophils, basophils, kinin and coagulation systems, and complement cascade).

A typical inflammatory response is characterized by (i) migration of leukocytes at the site of antigen (injury) localization; (ii) specific and nonspecific recognition of "foreign" and other (necrotic/injured tissue) antigens mediated by B and T lymphocytes, macrophages and the alternative complement pathway; (iii) amplification of the inflammatory response with the recruitment of specific and nonspecific effector cells by complement components, lymphokines and monokines, kinins, arachidonic acid metabolites, and mast cell/basophil products; and (iv) macrophage, neutrophil and lymphocyte participation in antigen destruction with ultimate removal of antigen particles (injured tissue) by phagocytosis. The ability of the immune system to discriminate between "self" and "non-self" (foreign) antigens is therefore vital to the functioning of the immune system as a specific defense against "non-self" antigens.

"Non-self" antigens are those antigens on substances entering a subject, or exist in a subject but are detectably different or foreign from the subject's own constituents, whereas "self" antigens are those which, in the healthy subject, are not detectably different or foreign from its own constituents. However, under certain conditions, including in certain disease states, an individual's immune system will identify its own constituents as "non-self," and initiate an immune response against "self-antigens," at times causing more damage or discomfort as from, for example, an invading microbe or foreign material, and often producing serious illness in a subject.

In another important embodiment, the inflammation is caused by an immune response against "self-antigen," and the subject in need of treatment according to the invention has an autoimmune disease. "Autoimmune disease" as used herein, results when a subject's immune system attacks its own organs or tissues, producing a clinical condition associated with the destruction of that tissue, as exemplified by diseases such as rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, systemic lupus erythematosus, etc.

Autoimmune disease may be caused by a genetic predisposition alone, by certain exogenous agents (e.g., viruses, bacteria, chemical agents, etc.), or both. Some forms of autoimmunity arise as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of a subject to antigens which are antigenically similar to, that is cross-reactive with, the subject's own tissue. In rheumatic fever, for example, an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta-cells of the islets of Langerhans), multiple sclerosis (involving the destruction of the conducting fibers of the nervous system) and rheumatoid arthritis (involving the destruction of the joint-lining tissue), are characterized as being the result of a mostly cell-mediated autoimmune response and appear to be due primarily to the action of T cells (See, Sinha et al., *Science*, 1990, 248:1380). Yet others, such as myesthenia gravis and systemic lupus erythematosus, are characterized as being the result of primarily a humoral autoimmune response. Nevertheless, inhibition of migration of immune cells to a specific site of inflammation involved in any of the foregoing conditions according to the invention, is beneficial to the subject since it inhibits escalation of the inflammatory response, protecting the specific site (e.g., tissue) involved, from "self-damage." In preffered embodiments, the subject has rheumatoid arthritis, multiple sclerosis, or uveitis.

In a further important embodiments, the inflammation is caused by an immune response against "non-self-antigens" (including antigens of necrotic self-material), and the subject in need of treatment according to the invention is a transplant recipient, has atherosclerosis, has suffered a myocardial infarction and/or an ischemic stroke, has an abscess, and/or has myocarditis. This is because after cell (or organ) transplantation, or after myocardial infarction or ischemic stroke, certain antigens from the transplanted cells (organs), or necrotic cells from the heart or the brain, can stimulate the production of immune lymphocytes and/or autoantibodies, which later participate in inflammation/rejection (in the case of a transplant), or attack cardiac or brain target cells causing inflammation and aggravating the condition (Johnson et al., *Sem. Nuc. Med* 1989, 19:238; Leinonen et al., *Microbiol. Path.*, 1990, 9:67; Montalban et al., *Stroke*, 1991, 22:750).

According to still another aspect of the invention, a method for enhancing mobilization of hematopoietic cells in a subject is provided. The method involves administering to a subject in need of such treatment a CaR receptor antagonist in an amount effective to enhance mobilization of hematopoietic cells in the subject. In certain embodiments, the CaR receptor antagonist is NPS-2143. In some embodiments, the hematopoietic cells are hematopoietic progenitor cells. In important embodiments, the hematopoietic cells are hematopoietic stem cells. In one embodiment, the subject is a bone marrow donor. By enhancing mobilization of bone marrow cells, the need for bone marrow isolation may be obviated. As a result of this mobilization, bone marrow cells (including hematopoietic stem cells) leave the bone marrow and enter the blood circulation of the subject undergoing such treatment with the agents of the invention. The circulating bone marrow cells can then be easily isolated using techniques well known in the art (for example, utilizing bone marrow cell-specific cell surface markers—e.g., CD34), and be transplanted into a different subject in need of bone marrow transplantation.

According to one aspect of the invention, a method of enhancing migration of CaR receptor expressing cells to a specific site in a subject is provided. The method involves, locally administering to a specific site in a subject in need of such treatment a nonCa$^{++}$ CaR receptor agonist in an amount effective to enhance migration of CaR receptor expressing cells to the specific site in the subject. In sonie embodiments, the specific site is a site of a pathogenic infection. In certain embodiments, the specific site is a germ cell-containing site. In further embodiments, the specific site is an area immediately surrounding a tumor. Efficient recruitment of immune cells to help eliminate the infection, unwanted germ-cell and/or tumor, is therefore beneficial.

In certain embodiments, the specific site is a germ cell containing site. In this case the recruitment of immune cells to these specific sites will help eliminate unwanted germ cells, and/or implanted and nonimplanted embryos. In further embodiments, co-administration of contraceptive agents other than anti-fugetactic agents is also provided. Non-CaR receptor agonist contraceptive agents are well known in the art.

In further embodiments, the specific site is an area immediately surrounding a tumor. Since most of the known tumors escape immune recognition, it is beneficial to enhance the migration of immune cells to the tumor site. In further embodiments, co-administration of anti-cancer agents other than CaR receptor agonists is also provided. Non-CaR receptor agonist anti-cancer agents include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Epothilones: Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin;

Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Taxanes such as Paclitaxel and Taxotere; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

According to a further aspect of the invention, a method for enhancing bone marrow engraftment following bone marrow transplantation, is provided. The method involves contacting isolated bone marrow cells to be transplanted with an agent that increases CaR receptor expression.

"Expression," as used herein, refers to nucleic acid and/or polypeptide expression, as well as to activity of the polypeptide molecule (e.g., ability to induce hematopoietic cell transmigration).

"Increased CaR receptor expression" or "Upregulation of CaR receptor expression," as used herein, refers to increased expression of the CaR gene and/or its encoded polypeptide. Increased expression refers to increasing (i.e., to a detectable extent) replication, transcription, and/or translation of any of the nucleic acids of the invention (CaR—SEQ ID No:1), since upregulation of any of these processes results in concentration/amount increase of the polypeptide encoded by the gene (nucleic acid). Conversely, "downregulation" or "decreased expression" refers to decreased expression of a gene and/or its encoded polypeptide. The upregulation or downregulation of gene expression can be directly determined by detecting an increase or decrease, respectively, in the level of mRNA for the gene, or the level of protein expression of the gene-encoded polypeptide, using any suitable means known to the art, such as nucleic acid hybridization or antibody detection methods, respectively, and in comparison to controls. Upregulation or downregulation of gene expression can also be determined indirectly by detecting a change, for example, in hematopoietic cell transmigration.

In some embodiments, an agent that increases CaR receptor expression is selected from the group consisting of $Ca^{++}$, Vitamin D, a chemokine, a CaR receptor agonist, and a CaR receptor nucleic acid (preferably one having the nucleotide sequence of SEQ ID NO:1).

The invention in certain aspects also embraces methods for modulating hematopoietic progenitor cell function. Such methods involve contacting a hematopoietic progenitor cell with an agent that modulates CaR receptor expression in an effective amount to modulate CaR receptor expression in the hematopoietic progenitor cell to modulate its function. In important embodiments, the agent that modulates CaR receptor expression is selected from the group consisting of $Ca^{++}$, Vitamin D, a chemokine, a CaR receptor agonist, a CaR receptor antagonist, a CaR receptor antisense agent, and a CaR receptor nucleic acid (see, e.g., SEQ ID NO:1).

As used herein, the term "CaR receptor antisense agent" refers to a CaR receptor "antisense oligonucleotide" or "antisense," which in turn describe an oligonucleotide that is an oligoribonucleotide, oligodeoxyribonucleotide, modified oligoribonucleotide, or modified oligodeoxyribonucleotide which hybridizes under physiological conditions to DNA comprising the CaR receptor gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med,* 1995, 1(11):1116-1118; Nat. Biotech., 1996, 14:840-844). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although, SEQ ID No:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID No:1. Similarly, antisense to allelic or homologous CaR receptor cDNAs and genomic DNAs are enabled without undue experimentation. In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding MIVR-1 polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

According to another aspect of the invention, a method for inducing hematopoietic progenitor cell quiescence, is provided. It has also been discovered, unexpectedly, that when a hematopoietic progenitor cell is contacted with an agent (in effective amounts) that increases CaR receptor expression in the hematopoietic stem cell, the hematopoietic stem cell becomes quiescent. A "quiescent progenitor cell" refers to a progenitor cell in the $G_1$ or $G_0$ phase of the cell cycle. A population of cells is considered herein to be a population of quiescent cells when at least 50%, preferably at least 70%, more preferably at least 80% of the cells are in the $G_1$ or $G_0$ phase of the cell cycle. Quiescent cells exhibit a single DNA peak by flow-cytometry analysis, a standard technique well known to those of ordinary skill in the arts of immunology and cell biology. Another technique useful for determining whether a population of cells is quiescent is the addition of a chemical agent to the cell culture medium that is toxic only to actively cycling cells, i.e., DNA synthesizing cells, and does not kill quiescent cells. Non-exclusive examples of such chemical agents include hydroxyurea and high specific activity tritiated thymidine ($^3$HtdR). A population of cells is evaluated as to the percent in an actively cycling state by the percent of the cell population killed by the chemical agent. A cell population in which in vitro tritiated thymidine killing is less than approximately 30%, preferably less than approximately 10%, more preferably less than approximately 5%, is considered to be quiescent.

According to another aspect of the invention, a method for inhibiting hematopoietic progenitor cell-death is provided, particularly when the hematopoietic progenitor cell is subjected to an environmental stress. The method involves inducing hematopoietic progenitor cell quiescence by contacting the cell with an agent that increases CaR receptor expression in the hematopoietic progenitor cell prior to or during the application of the stress, both in vivo and in vitro. The lifespan of a hematopoietic progenitor cell (or any other mammalian cell) under environmental stress is significantly shorter when compared to the lifespan of a hematopoietic stem cell under no such stress. This can be easily detected by placing a number of cells under a form of environmental stress and comparing their survival (numbers) to an identical number of cells free from any stress over a period of time. The amount of the foregoing agent(s) of the invention sufficient to inhibit cell-death, is the amount sufficient to extend the lifespan of the hematopoietic progenitor cell under environmental stress toward comparable lifespan lengths of hematopoietic progenitor cells free from any environmental stress. Such methods can be used to protect cells from environmental insults, such as increased temperatures (e.g., fever), physical, trauma, oxidative, osmotic and chemical stress(e.g. a chemotherapeutic agent), and UV irradiation.

According to a further aspect of the invention, a method of inhibiting tumor cell metastasis in a subject, is provided. The method involves locally administering to a tumor site in a subject in need of such treatment a CaR receptor agonist in an amount effective to inhibit metastasis of tumor cells from the tumor site in the subject. In further embodiments, the method involves co-administering a cytokine binding agent. In some embodiments, the cytokine binding agent is an anti-cytokine antibody or a cytokine agonist. Antibodies are as described earlier in relation to CaR receptor agonist binding agents except that they selectively bind a cytokine. Preferred cytokines are as described elsewhere herein. In further embodiments, co-administration of anti-cancer agents other than CaR receptor agonists is also provided. Anti-cancer agents are as described above.

According to another aspect of the invention, a method of inhibiting endothelial cell migration to a tumor site in a subject, is provided. The method involves locally administering to an area surrounding a tumor site in a subject in need of such treatment a CaR receptor antagonist in an amount effective to inhibit endothelial cell migration to the tumor site in the subject (to prevent angiogenesis and/or metastasis). In certain embodiments, the area surrounding the tumor site is not immediate to the tumor site. Important fugetactic agents are as described above.

The tumor cell may be of a cancer or tumor type thought to escape immune recognition. Such cancers or tumors may be of the folowing origin: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In any of the foregoing embodiments, the CaR receptor expressing cell is a hematopoietic cell. In preferred embodiments, the hematopoietic cell is an immune cell. In important embodiments, the hematopoietic cell is hematopoietic progenitor cell.

The foregoing methods of therapy may include co-administration of a non-CaR receptor related agent together with a CaR receptor related agent (CaR receptor antagonist—including $Ca^{++}$-, or antagonist) of the invention that can act cooperatively, additively, or synergistically with the CaR receptor related agent of the invention to modulate migration of CaR expressing cells (e.g., immune cells) to or from a site of inflammation in the subject. "Co-administering," as used herein, refers to administering simultaneously two or more compounds of the invention (e.g., a CaR receptor related agent and a non-CaR receptor related agent), as an admixture in a single composition, or sequentially, close enough in time so that the compounds may exert an additive or even synergistic effect, i.e., to modulate migration of CaR expressing cells to or from a site of inflammation.

In certain embodiments, the non-CaR receptor related agents are immunosuppressants. Such immunosuppressants include: Azathioprine; Azathioprine Sodium; Cyclosporine; Daltroban; Gusperimus Trihydrochloride; Sirolimus; Tacrolimus.

In other embodiments, the non-CaR receptor related agents are anti-inflammatory agents. Such anti-inflammatory agents include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

According to a further aspect of the invention, a method for treating a subject to enhance immune reactivity toward a specific antigen in the subject, is provided. The method involves administering to a subject in need of such treatment an amount of a CaR receptor agonist together with an amount of a specific antigen, wherein the amount of the CaR receptor agonist is sufficient to enhance in the subject immune reactivity toward the specific antigen versus the same amount of the specific antigen if administered without the a CaR receptor agonist. By administering a CaR receptor agonist "together with" a specific antigen, it is meant that the two agents are administered at the same time, preferably admixed together in a single composition (e.g., the CaR receptor agonist is acting as adjuvant);

A "specific antigen", as used herein, falls into four classes: 1) antigens that are characteristic of a pathogen; 2) antigens that are characteristic of an autoimmune disease; 3) antigens that are characteristic of an allergen; and 4) antigens that are characteristic of a tumor. Antigens in general include polysaccharides, glycolipids, glycoproteins, peptides, proteins, carbohydrates and lipids from cell surfaces, cytoplasm, nuclei, mitochondria and the like.

Antigens that are characteristic of pathogens include antigens derived from viruses, bacteria, parasites or fungi. Examples of important pathogens include *vibrio* choleras, enterotoxigenic *Escherichia coli*, rotavirus, *Clostridium difficile, Shigella* species, *Salmonella typhi*, parainfluenza virus, influenza virus, *Streptococcus pneumonias, Borella burgdorferi*, HIV, *Streptococcus mutans, Plasmodium falciparum, Staphylococcus aureus*, rabies virus and Epstein-Barr virus.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae; and viruses including, but not limited to, cytomegalovirus; Hepatitis A, B, C, D, E; Herpes simplex virus types 1 & 2; Influenzae virus; Mumps virus; Parainfluenza 1, 2 and 3; Epstein Barr virus; Respiratory syncytial virus; Rubella virus; Rubeola virus; Varicella-zoster virus; *Vibrio Cholerae*; Human immunodeficiency viruses (HIVs) and HIV peptides, including HIV-1 gag, HIV-1 env, HIV-2 gag, HIV-2 env, Nef, RT, Rev, gp120, gp41, p15, p17, p24, p7-p6, Pol, Tat, Vpr, Vif, Vpu; Hantavirus; Ebola virus; Lymphocytic ChorioMeningitis virus; Dengue virus; Rotavirus; Human T-lymphotropic (HTLV-I); HTLV-II; Human herpesvirus-6 (HHV-6); HHV-8; Guanarito virus; *Bartonella henselae*; Sin nombre virus; and Sabia virus. Exemplary cytomegalovirus epitopes include GP 33-43, NP396-404, and GP276-286. An exemplary influenza epitope includes the HA peptide.

Bacteria in general include but are not limited to: *P. aeruginosa; Bacillus anthracis; E. coli, Enterocytozoon bieneusi; Klebsiella* sp.; *Klebsiella pneumoniae; Serratia* sp.; *Pseudomonas* sp.; *P. cepacia; Acinetobacter* sp.; *S. epidermis; E. faecalis; S. pneumoniae; S. aureus; Haemophilus* sp.; *Haemophilus Influenza; Neisseria* Sp.; *Neisseria gonorheae; Neisseria meningitis; Helicobacter pylori; Bacteroides* sp.; *Citrobacter* sp.; *Branhamella* sp.; *Salmonella* sp.; *Salmonella typhi; Shigella* sp.; *S. pyogenes; Proteus* sp.; *Clostridium* sp.; *Erysipelothrix* sp.; *Lesteria* sp.; *Pasteurella multocida; Streptobacillus* sp.; *Spirillum* sp.; *Fusospirocheta* sp.; *Actinomycetes; Mycoplasma* sp.; *Chlamydiae* sp.; *Chlamydia trachomatis; Campylobacter jejuni; Cyclospora cayatanensis; Rickettsia* sp.; Spirochaeta, including *Treponema pallidum* and *Borrelia* sp.; *Legionella* sp.; *Legionella pneumophila; Mycobacteria* sp.; *Mycobacterium tuberculosis; Ureaplasma* sp.; *Streptomyces* sp.; *Trichomonas* sp.; and. *P. mirabilis*, as well as toxins, that include, but are not limited to, Anthrax toxin (EF); Adenylate cyclase toxin; Cholera enterotoxin; *E. coli* LT toxin; *Escherichia coli* 0157:H7; Shiga toxin; Botulinum Neurotoxin Type A heavy and light chains; Botulinum Neurotoxin Type B heavy and light chains; Tetanus toxin; Tetanus toxin C fragment; Diphtheria toxin; Pertussis toxin; Parvovirus B19; *Staphylococcus* enterotoxins; Toxic shock syndrome toxin (TSST-1); Erythrogenic toxin; and *Vibrio cholerae* 0139.

Parasites include but are not limited to: *Ehrlichia chafeensis; Babesia; Encephalitozoon cuniculi; Encephalitozoon hellem; Schistosoms; Toxoplasma gondii; Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidum parvum; Pneumocytis carinii, Babesia bovis, B. divergens, B. microti, Isospore belli, L hominis; Dientamoeba fragiles; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirius pubis*; and *Dermatobia hominis*.

Fungi in general include but are not limited to: *Cryptococcus neoformans; Blastomyces dermatitidis; Aiellomyces dermatitidis; Histoplasfria capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata*; and *Dermatophyres* species.

Antigens that are characteristic of autoimmune disease typically will be derived from the cell surface, cytoplasm, nucleus, mitochondria and the like of mammalian tissues. Examples include antigens characteristic of uveitis (e.g. S antigen), diabetes mellitus, multiple sclerosis, systemic lupus erythematosus, Hashimoto's thyroiditis, myasthenia gravis, primary myxoedema, thyrotoxicosis, rheumatoid arthritis, pernicious anemia, Addison's disease, scleroderma, autoimmune atrophic gastritis, premature menopause (few cases), male infertility (few cases), juvenile diabetes, Goodpasture's syndrome, pemphigus vulgaris, pemphigoid, sympathetic opthalmia, phacogenic uveitis, autoimmune haemolytic anemia, idiopathic thrombocylopenic purpura, idiopathic feucopenia, primary biliary cirrhosis (few cases), ulcerative colitis, Siogren's syndrome, Wegener's granulomatosis, poly/dermatomyositis, and discold lupus erythromatosus.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include the urushiols (pentadecylcatechol or heptadecyicatechol) of Toxicodendron species such as poison ivy, poison oak and poison sumac, and the sesquiterpenoid lactones of ragweed and related plants.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and tumor mucins and glycolipids. Tumors include, but are not limited to, those from the following sites of cancer and types of cancer: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogeneous leukemia; multiple myeloma; AIDS associates leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basal cell cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. Viral proteins associated with tumors would be those from the classes of viruses noted above. Antigens characteristic of tumors may be proteins not usually expressed by a tumor precursor cell, or may be a protein which is normally expressed in a tumor precursor cell, but having a mutation characteristic of a tumor. An antigen characteristic of a tumor may be a mutant variant of the normal protein-having an altered activity or subcellular distribution. Mutations of genes giving rise to tumor antigens, in addition to those specified above, may be in the coding region, 5' or 3' noncoding regions, or introns of a gene, and may be the result of point mutations frameshifts, deletions, additions, duplications, chromosomal rearrangements and the like. One of ordinary skill in the art is familiar with the broad variety of alterations to normal gene structure and expression which gives rise to tumor antigens.

Specific examples of tumor antigens include: proteins such as Ig-idiotype of B cell lymphoma, mutant cyclin-dependent kinase 4 of melanoma, Pmel-17 (gp 100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma; carbohydrate/lipids such as muci mucin of breast, pancreas, and ovarian cancer, GM2 and GD2 gangliosides of melanoma; oncogenes such as mutant. p53 of carcinoma, mutant ras of colon cancer and HER21neu proto-onco-gene of breast carcinoma; viral products such as human papilloma virus proteins of squamous cell cancers of cervix and esophagus; and antigens (shown in parenthesis) from the following tumors: acute lymphoblastic leukemia (etv6; amll; cyclophilin b), glioma (E-cadherin; α-catenin; α-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)-C017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), hodgkins lymphoma (Imp-1; EBNA-1), lung cancer (CEA; MAGE-3; NY-ESO-1), lymphoid cell-derived leukemia (cyclophilin b), myeloma (MUC family; p21ras), non-small cell lung carcinoma (HER2/neu; c-erbB-2), nasopharyngeal cancer (lmp-1; EBNA-1), ovarian cancer cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), testicular cancer (NY-ESO-1), T cell leukemia (HTLV-1 epitopes), and melanoma (Melan-AIMART-1; cdc27; MAGE-3; p21ras; gp100$^{Pmel117}$). It is also contemplated that proteinaceous tumor antigens may be presented by HLA molecules as specific peptides derived from the whole antigenic protein. Metabolic processing of proteins to yield antigenic peptides is well known in the art; for example see U.S. Pat. No. 5,342,774 (Boon et al.). and the ones on the lists previously.

Antigens may also include: C reactive protein; Coxsackie B1, B2, B3, B4, EI5, B6 proteins; Myelin basic protein; pancreatic beta-cell antigens; arthritis associated antigens (cartilage, aggrecan, type II collagen); AP-1; NF-kappaB; desmoglein (Dsg 1 or 3); and alzheimer's associated antigens (prions, amyloid-beta protein), and/or any synthetic agent that binds to the T-cell receptor.

In certain embodiments, the method according to this aspect of the invention further comprises co-administering a non-CaR receptor agonist adjuvant. A "non-CaR receptor agonist adjuvant," as used herein, refers to an agent that augments, stimulates, activates, potentiates, or modulates the immune response at either the cellular or humoral level. As a result, less vaccine (specific antigen) may be used to produce an immune response toward the antigen. Well known immunologic adjuvants include Freund's adjuvant, bcg, and *corynebacterium parvum*. In important embodiments, the non-CaR receptor agonist adjuvant is Freund's incomplete adjuvant. Freund's incomplete adjuvant is prepared by mixing 9 parts Marcol 52 (a white mineral oil of national formulary grade with a viscosity of not more than 37 centistokes at 100 degree F., and a specific gravity range of 0.818 to 0.880 at 77 degree F.) and 1 part of Arlacel A (mannide monoleate, purest grade for use in human and veterinary adjuvant formulations) and filtering through a 0.45μ filter.

According to another aspect of the invention, a method for treating a subject to enhance immune tolerance in the subject, is provided. The method involves administering to a subject in need of such treatment an amount of a CaR receptor antagonist, wherein the amount of the CaR receptor antagonist is sufficient to enhance in the subject immune tolerance to a self or a non-self antigen. Important CaR receptor antagonists are as described above. In certain embodiments, the subject has an autoimmune disease. In preferred embodiments, the autoimmune disease includes rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, systemic lupus erythematosus. In further embodiments, the subject has multiple sclerosis, an abscess, a transplant, an implant, atherosclerosis, and/or myocarditis.

The compositions, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a local (site-specific) reduction of inflammation. In other cases, it is inhibition of tumor growth and/or metastasis. In further cases it is mobilization of stem cells.

Generally, doses of active compounds of the present invention would be from about 0.01 mg/kg per day to 1000 mg/kg per day. It is expected that doses ranging from 50-500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent.

Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The CaR receptor related agents (CaR receptor agonists—including $Ca^{++}$-, or antagonists), may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The invention in other aspects includes pharmaceutical compositions of CaR receptor related agents.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

CaR receptor related agents that are nucleic acid or peptide molecules (e.g., CaR peptide) preferably are produced recombinantly, although such molecules may be isolated from biological extracts. Recombinantly produced CaR receptor related agents such as CaR peptides (ligands for the CaR receptor), include chimeric proteins comprising a fusion of a CaR peptide with another polypeptide, e.g., a polypeptide capable of providing or enhancing protein-protein binding, sequence specific nucleic acid binding (such as GAL4), enhancing stability of the CaR peptide under assay conditions, or providing a detectable moiety, such as green fluorescent protein. A polypeptide fused to a CaR peptide or fragment may also provide means of readily detecting the fusion protein, e.g., by immunological recognition or by fluorescent labeling. The CaR receptor related agent (if a polypeptide) can be administered as a polypeptide, and/or a nucleic acid which expresses the polypeptide.

Various techniques may be employed for introducing nucleic acids of the invention (CaR peptide sense and antisense, CaR receptor dominant negative, etc.) into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the CaR related agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., *Trends Biochem. Sci.*, (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In one important embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the CaR receptor related agents described herein are encapsulated or dispersed within the biocompatible, preferably biodegradable polymeric matrix disclosed in PCT/US/03307.

The polymeric matrix preferably is in the form of a microparticle such as a microsphere (wherein a CaR receptor related agent is dispersed throughout a solid polymeric matrix) or a microcapsule (wherein a CaR receptor related agent is stored in the core of a polymeric shell). Other forms of the polymeric matrix for containing a CaR receptor related agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and CaR receptor related agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng.*, 1996, 52:96-101, and Mathiowitz et al., *Nature*, 1997, 386:410-414.

Both non-biodegradable and biodegradable polymeric matrices can be used to deliver the CaR receptor related agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

CaR receptor related agents can be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, et al., in *Macromolecules*, 1993, 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr., et al.,

*Nature*, 1999, 397:335-338, the contents of which are expressly incorporated herein by reference.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In certain embodiments, the isolated CaR receptor related agents of the invention are delivered directly to the site at which there is inflammation, e.g., the joints in the case of a subject with rheumatoid arthritis, the blood vessels of an atherosclerotic organ, etc. For example, this can be accomplished by simple injection, or by attaching an isolated CaR receptor related molecule (agonist/antagonist) to the surface of a balloon catheter; inserting the catheter into the subject until the balloon portion is located at the site of inflammation, e.g. an atherosclerotic vessel, and inflating the balloon to contact the balloon surface with the vessel wall at the site of the occlusion. In this manner, the compositions can be targeted locally to particular inflammatory sites to modulate immune cell migration to these sites. In another example the local administration involves an implantable pump to the site in need of such treatment. Preferred pumps are as described above. In a further example, when the treatment of an abscess is involved, the CaR receptor related agent may be delivered topically, e.g., in an ointment/dermal formulation. Optionally, the CaR receptor related agents of the invention are delivered in combination with a non-CaR receptor related agents (e.g., antiinflammatory, immunosuppressant, etc.).

In a preferred embodiment of the invention, the isolated CaR receptor related agents of the invention are administered to a subject in combination with a balloon angioplasty procedure. A balloon angioplasty procedure involves inserting a catheter having a deflated balloon into an artery. The deflated balloon is positioned in proximity to the atherosclerotic plaque and the site of inflammation, and is inflated such that the plaque is compressed against the arterial wall. As a result, the layer of endothelial cells on the surface of the artery is disrupted, thereby exposing the underlying vascular smooth muscle cells. The isolated CaR receptor related molecule is attached to the balloon angioplasty catheter in a manner which permits release of the isolated CaR receptor related molecule at the site of the atherosclerotic plaque and the site of inflammation. The isolated CaR receptor related agent may be attached to the balloon angioplasty catheter in accordance with standard procedures known in the art. For example, the isolated CaR receptor related agent may be stored in a compartment of the balloon angioplasty catheter until the balloon is inflated, at which point it is released into the local environment. Alteratively, the isolated CaR receptor related agent may be impregnated on the balloon surface, such that it contacts the cells of the arterial wall as the balloon is inflated. The CaR receptor related agent also may be delivered in a perforated balloon catheter such as those disclosed in Flugelman, et al., *Circulation*, 1992, 85:1110-1117. See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid to the balloon angioplasty catheter.

The invention will be more fully understood by reference to the following examples. These examples, however, are merely intended to illustrate the embodiments of the invention and are not to be construed to limit the scope of the invention.

EXAMPLES

Materials and Methods

Preparation of peripheral blood CD14$^+$ monocytes. Low density cells were isolated from human and mouse peripheral blood using Ficoll-Hypaque (Pharmacia, Piscataway, N.J.). CD14$^+$ monocytes were purified by sorting on FACSVantage (Becton Dickinson, San Jose, Calif.) based on CD14 expression. Purified cells were incubated in either calcium-free medium (Hanks' Balanced Salt Solution 1×, CellGro, Hermdon. VA) or Iscove's Medium 1×(Mod) (CellGro, Herndon, Va.) which contains 1.5 mM Ca++. The medium was subsequently supplemented with 0.5 mM, 1 mM, 2 mM, 3 mM or 5 mM calcium chloride ($CaCl_2$) (Sigma) to achieve the desired level of extracellular calcium, or with 1 μM of the selective CaR activator, NPS R-467, or its less active stereoisomer, NPS S-467, in 3 mM Ca$^{++}$ (NPS Pharmaceuticals, Inc., Salt Lake City, Utah). Cells were incubated for up to 24 hours in 5% $CO_2$ humidified air. Monocytes were then detached from the plate using a cell scraper. All calcium concentrations indicated in the presentation of the data represent the total Ca$^{++}$ present in the basal medium plus any added Ca$^{++}$.

Transmigration assays. Transwells (5 μm pore size polycarbonate membrane, 12 mm diameter) (Costar, Corning, N.Y.) were used to assess cell migration using an established methodology (25). The concentration of Ca$^{++}$ in IMDM (CellGro, Herndon, Va.) in the upper and lower chambers of the transwell were adjusted according to a checkerboard analysis of chemotaxis. Calcium concentrations varied from 0 mM to 6.5 mM. Purified monocytes (1×10$^4$) were then placed in the top chamber with 150 μl of IMDM (CellGro, Hemdon, Va.). 500 μl of the medium was added to the bottom of the well and supplemented with varying concentrations of Ca$^{++}$ or with Ca$^{++}$ plus 10 ng/ml of MCP-1, 100 ng/ml of SDF-1α or 10 ng/ml of MIP-1α (PeproTech, Rocky Hills, N.Y.). Cells were incubated at 37° C. for 3 hours. To study inhibition of chemotaxis, cells were subsequently incubated with wortmannin (1 μM for 20 minutes at 37° C.), herbimycin (1 μM for 20 minutes at 37° C.) or genistein (1 μg/ml for 20 minutes at 37° C.), before their use in transmigration assays. At the end of the experiment, cells were then harvested from the lower chamber and counted using a hemocytometer.

Cytosolic calcium changes. Purified monocytes were loaded with Indo-1/AM (Molecular Probes, Eugene, Oreg.). Cells were collected on FACSVantage for 0.30 sec to establish a baseline emission value for Indo-1/AM. Chemokine ligands were then added to cells incubated in Ca$^{++}$-free media, or those supplemented with 1.5 mM, or 4.5 mM $CaCl_2$, or with the selective calcium receptor activator, NPS R-467, or the less active S-467 (1 μM) (A gift of E. Nemeth, NPS Pharmaceuticals, Inc. Salt Lake City, Utah). Data acquisition then continued for up to 5 minutes.

Chemokine receptor expression and flow cytometric analysis. Purified monocytes were incubated in a Ca$^{++}$-free medium supplemented with 1 mM, 3 mM or 5 mM $CaCl_2$ or with 1.5 mM $CaCl_2$ plus 1 μM NPS R-467 or S-467. Cells were washed once in PBS with 1% FCS and resuspended in 100 μl of Ca$^{++}$-free PBS. Monoclonal antibody against the CaR was added to the cells and incubated alone or with the CaR peptide for 30 min at room temperature. Cells were washed with PBS containing 1% FCS, resuspended in PBS with 1% FCS and incubated for 15 min at room temperature with anti-mouse IgG conjugated to FITC. The cells were washed again and conjugated monoclonal antibody [anti-CXCR4, anti-CCR5 (Pharmingen, San Diego, Calif.); anti-CCR2 (R&D, Minneapolis, Minn.); anti-CD14 (Becton Dickinson, San Jose, Calif.); or anti-CD4 (Becton Dickinson, San Jose, Calif.)] was added and incubated for 15 min at room temperature. Stained cells were fixed with 1% paraformaldehyde and assayed within 24 hrs. Flow cytometric analysis was performed using a dual laser FACSCalibur (Becton Dickinson Immunocytometry Systems, San Jose, Calif.) calibrated using 2 μm Calibrite beads (Becton Dickinson). Data acquisition and analysis were performed using CellQuest software (Becton Dickinson).

Breeding and genotyping of CaR −/− mice

CaR−/− were bred as previously described (Ho, C., et al., *Nat Genet* 1995, 11:389-94). To produce CaR−/− mice for this study, heterozygote mice were intercrossed. The mice studied were either 129S6/svev or 129S6/svev/Swiss Webster mixed genetic background. Mice homozygous for the CaR knockout allele do not live longer than three weeks. Mice were genotyped using the following protocol. A 1 μl sample of DNA sample was obtained from a <5 mm section of the tail of each mouse to be genotyped by according to established techniques[19]. In this way the genotype of CaR −/−, +/− and +/+ mice were obtained. Peripheral blood was obtained from each genotype of mouse at sacrifice at day 6 to 8 post partum.

Biologic activity of ionic calcium in vivo. C57BL/6 mice (Jackson Laboratories) were injected subcutaneously at a marked, shaved spot on the abdomen with 20 μl of 5 mM $CaCl_2$ or 20 μl of MCP-1 at a concentration of 10 ng/ml, with a combination of MCP-1 and 5 mM $CaCl_2$ or with 10 μM NPS R-467 in PBS. Control mice were injected subcutaneously with 20 μl PBS alone. All subcutaneously injected agents contained less than 0.004 ng/ml of LPS by the *limulus* assay (Sigma) as previously described (Bleul, C. C., et al., *J Exp Med,* 1996, 184:1101-1109). Mice were sacrificed by $CO_2$ asphyxiation 18 hours after injection, and injection sites were excised, snap-frozen and 4 μm cryosections were obtained and stained with hematoxylin and eosin. Immunocytochemistry was performed on the frozen sections using alkaline phosphatase-conjugated Mac-1 antibody (Pharmingen) as previously described and assessed by light microscopy (Bleul, C. C., et al., supra).

Example 1

Calcium mobilization and chemotaxis. Combining flow cytometry results with our prior data showing the presence of CaR mRNA and protein in monocytes by RT-PCR and Western analysis we demonstrated that the CaR is expressed on the cell surface of peripheral blood monocytes (FIG. 1*a*). We next examined the CaR's functional relevance in monocytes. Extracellular $Ca^{++}$ increased the cytosolic $Ca^{++}$ concentration in a dose dependent manner with a maximal response at 4.5 mM $Ca^{++}$ (FIG. 1*b*), consistent with the receptor's known capacity to elevate cytosolic calcium by activating PLC.

Figure 2A:
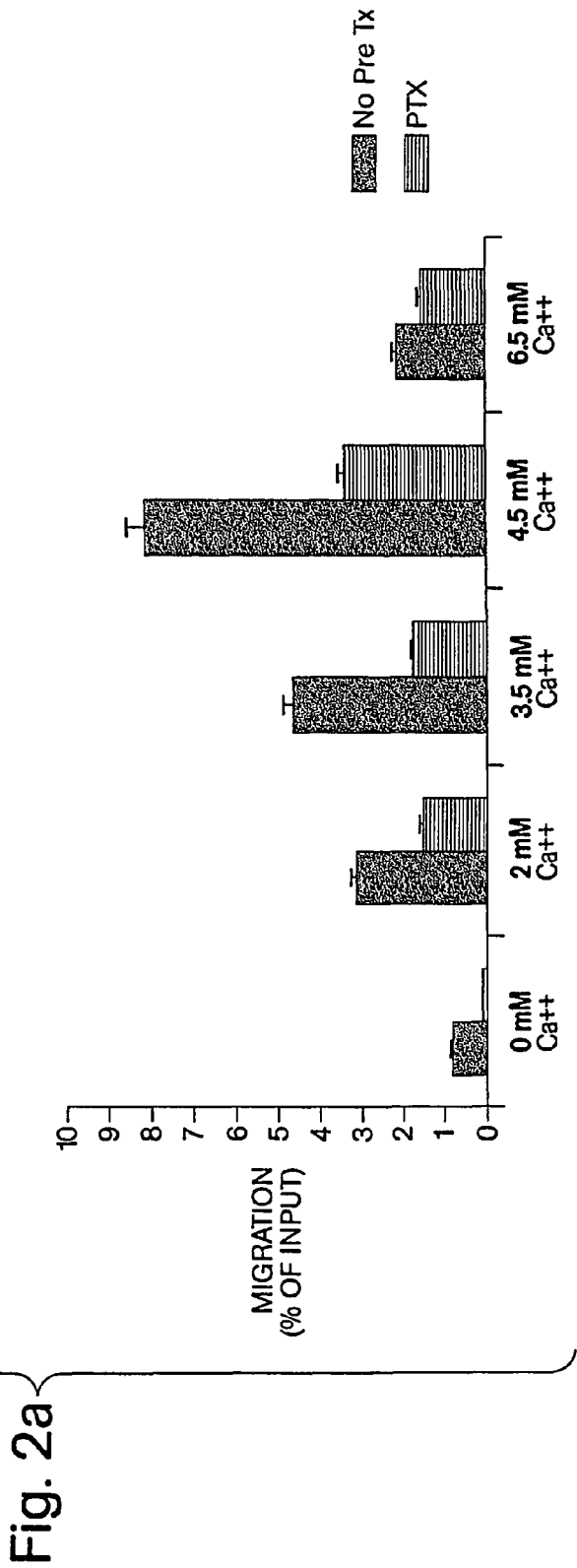
FIG. 2(a)—upper panel: checkerboard analysis for transmigration assays were used to determine if Ca$^{++}$ was capable of inducing monocyte chemotaxis FIG. 2(a)—lower panel: bar graph showing a Ca$^{++}$ dose dependent effect.
Figure 2B:
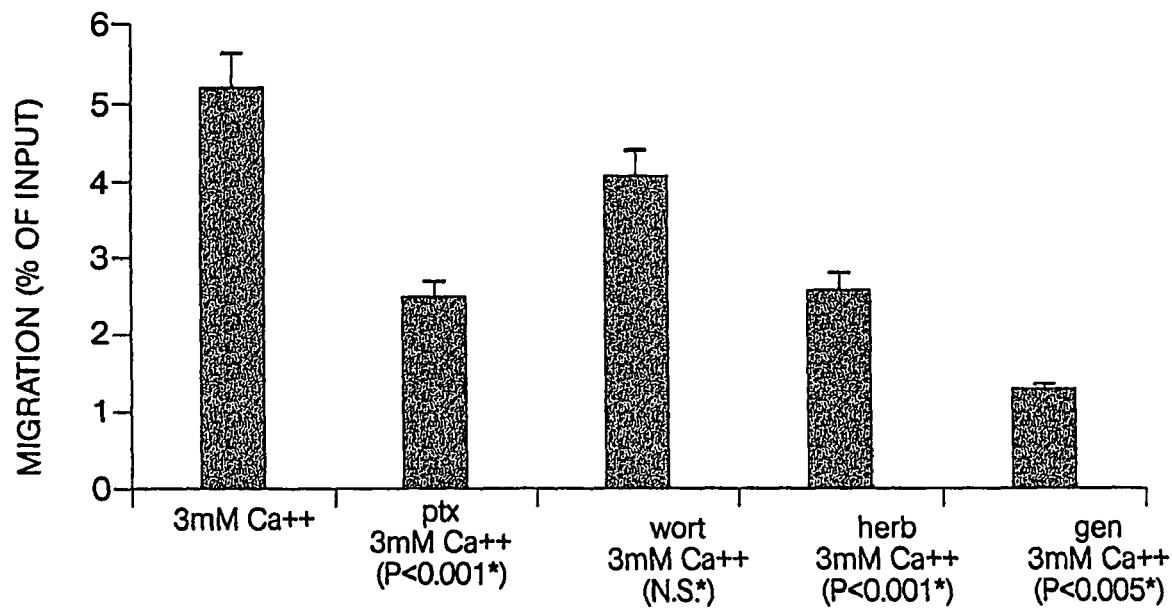
FIG. 2(b): bar graph showing chemotaxis of monocytes towards a positive gradient of Ca$^{++}$ that is inhibitable by pretreatment with the tyrosine kinase inhibitors, genistein (gen) or herbimycin (herb), but not by the PI-3 kinase inhibitor, wortmannin (wort)
Figure 2C:
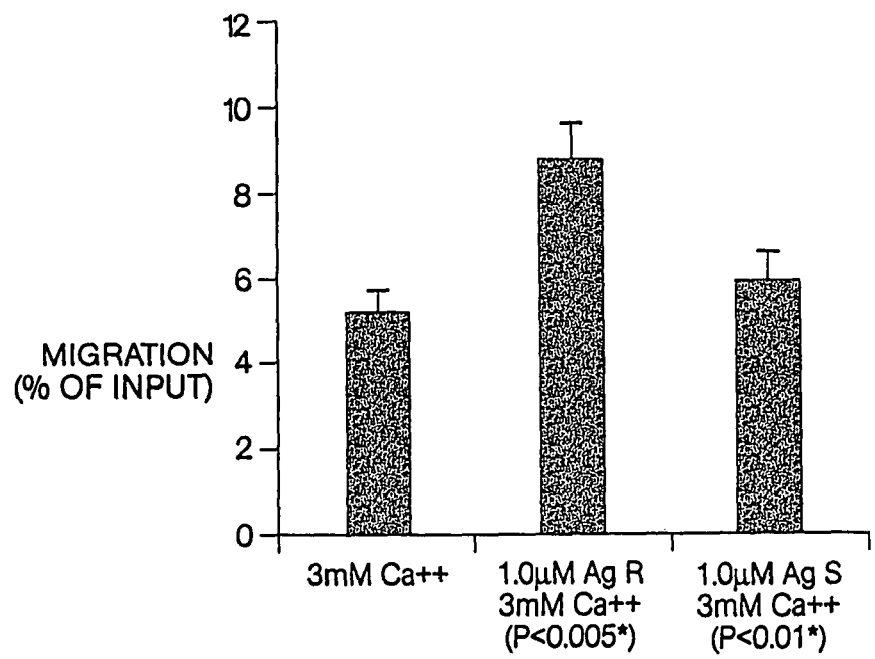
FIG. 2(c): bar graphs depicting the role of the CaR in mediating the chemotactic response to elevated Ca$^{++}$.

A transmigration assay was then used to determine if calcium was capable of inducing monocyte chemotaxis. A dose dependent effect was seen with maximal chemotaxis observed at 4.5 mM $Ca^{++}$ in a checkerboard analysis of chemotaxis to varying concentration gradients of ionic calcium, which was inhibitable by PTX, the tyrosine kinase inhibitors, herbimycin and genistein, but not by the PI-3 kinase inhibitor, wortmannin. (FIG. 2*a*, 2*b*). The role of the CaR in these responses was further assessed by exposure of the cells to spermine, a polycationic CaR agonist (Quinn, S. J., et al., *Am J Physiol,* 1997, 273:C1315-23), the selective CaR activator, NPS R-467, or its less active stereoisomer, NPS S-467 (courtesy of Dr. E. Nemeth, NPS Pharmaceuticals, Inc., Salt Lake City, Utah) (Nemeth, E. F., et al., *Proc Natl Acad Sci USA,* 1998, 95:4040-5; Chattopadhyay, N., et al., Glia, 26:64-72). Stimulation of cytosolic calcium responses and transmigration were noted with each of these agents. The greater potency of R-467 vs. S-467 in enhancing the actions of high $Ca^{++}$ on these two biological responses is fully in accord with their known pharmacological actions on the cloned CaR and strongly support the receptor's role in mediating these actions of extracellular $Ca^{++}$ on monocytes (Nemeth, E. F., et al., *Proc Natl Acad Sci USA,* 1998, 95:4040-5) (FIG. 2*c*).

Figure 2D:
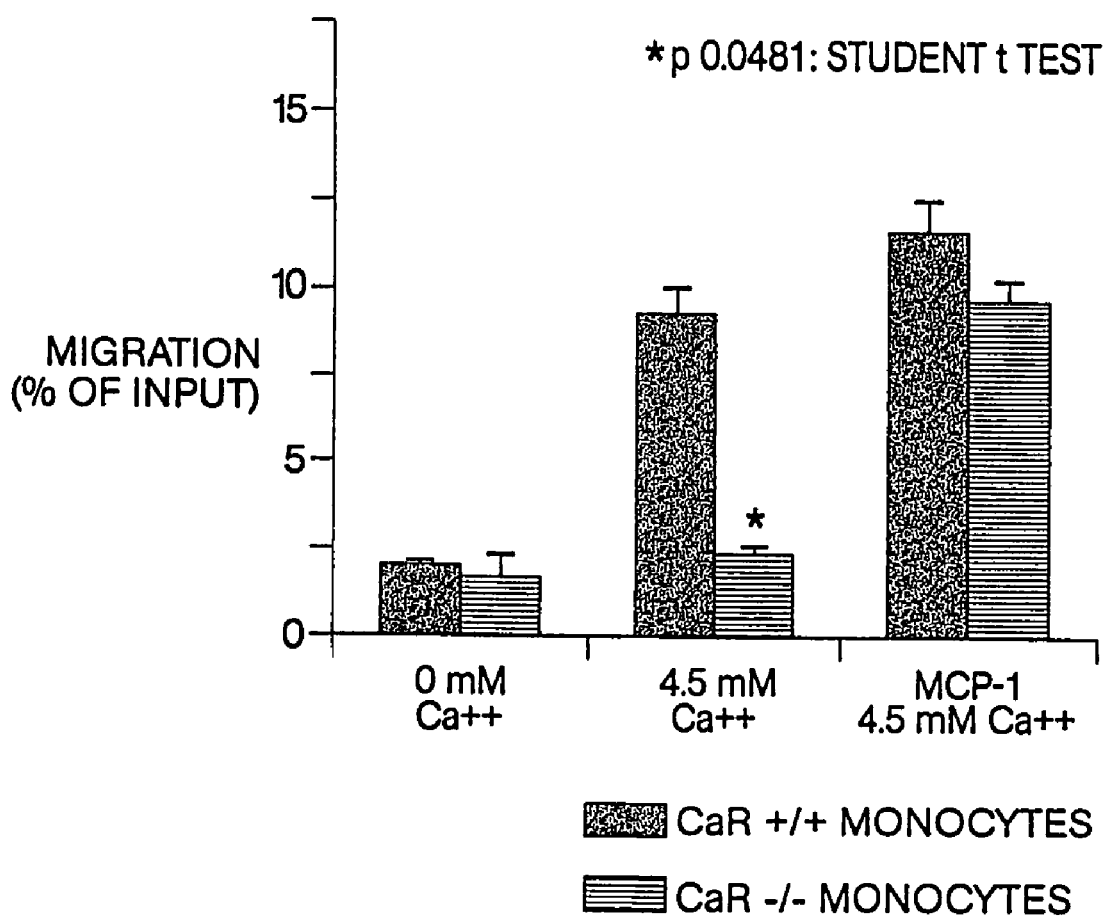
FIG. 2(d): bar graphs showing chemotaxis of peripheral blood monocytes obtained from CaR−/− and CaR+/+ mice in response to 4.5 mM Ca$^{++}$ and to MCP-1 in the presence of 1.5 mM Ca$^{++}$.

To confirm the CaR role in mediating the chemotaxis induced by a calcium gradient, we examined mononuclear cells derived from neonatal CaR −/−, +/− or +/+ mice. The cells were capable of chemotaxing to MCP-1, however, −/− cells failed to transmigrate to the $Ca^{++}$ gradient (FIG. 2*d*) thereby definitively demonstrating the role of the CaR in the response.

Figure 2E:
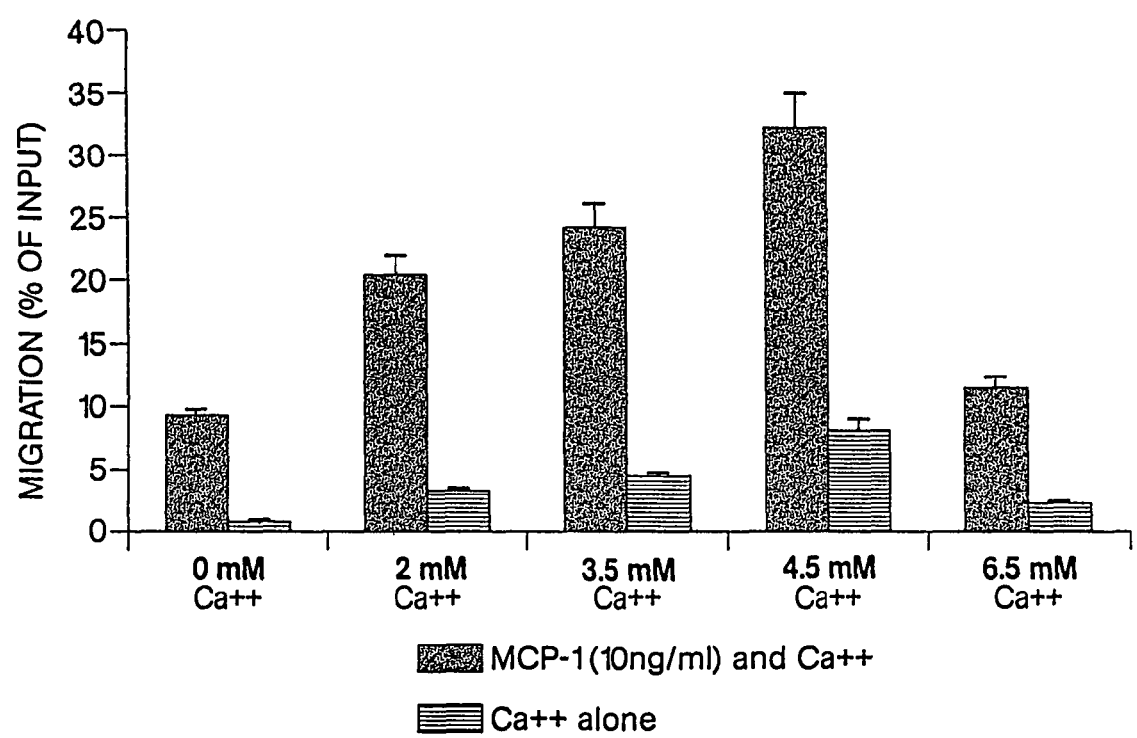
FIG. 2(e): bar graphs showing the percent migration of CaR +/+monocytes (solid bars) and CaR−/− monocytes (striped bars).

Chemokine receptor interactions. We next evaluated whether calcium interacted with other regulators of monocyte migration, assessing the co-expression of chemokine receptors and the CaR on primary human adult monocytic cells. CCR-2 and CCR-5 were present on 100% of $CD14^+$ PBMC, and CXCR-4 was present on 87%; co-expression of the CaR with CCR2 was noted in 97% of $CD14^+$ PBMC and in 83% with CXCR4. Functional responses of monocytes to activation of receptors for chemokines were then measured in the presence or absence of CaR stimulation using transmigration assays. Chemotaxis of $CD14^+$ PBMC to a positive concentration gradient of MCP-1 was dependent upon extracellular calcium, as has been reported by others (Sozzani, S., et al, *J Immunol,* 1991, 147:2215-21; Sozzani, S., et al., *J Immunol* 1993, 150:1544-53), while MIP-1α and SDF-1α induced migration independent of calcium. The percent of cells migrating in response to MCP-1 could be augmented by raising extracellular $Ca^{++}$, with peak activity noted at 4.5 mM $Ca^{++}$ (FIG. 2*e*). The increase in transmigration elicited by a combination of MCP-1 and elevated $Ca^{++}$ concentrations was greater than the sum of transmigration evoked by either MCP-1 or $Ca^{++}$ alone, indicating the synergistic nature of the interaction. In contrast, no synergistic effect was noted when either MIP-1α or SDF-1α was used in conjunction with added $Ca^{++}$.

The mechanism by which $Ca^{++}$ enhanced responsiveness to MCP-1 was evaluated by assessing receptor expression kinetics following CaR stimulation. Exposure of cells to elevated $Ca^{++}$ resulted in up-modulation of cell surface CCR-2 at 3 hours (Table 1L). In contrast, antibodies directed against CCR-5 failed to demonstrate any change in median fluorescence intensity, while CXCR-4 expression increased but did not achieve statistical significance. Similarly, the fluorescence intensity of anti-CD4 antibody staining did not vary with Cam concentration thereby excluding a non-specific enhancement of antibody staining in the presence of increased calcium. Inhibition of new protein synthesis by cyclohexamide had no effect on the $Ca^{++}$-mediated upregulation of CCR-2, indicating that $Ca^{++}$ altered receptor processing and/or trafficking between cell surface and intracellular pools, rather than the generation of new receptor molecules.

In order to assess whether there was reciprocal regulation of the CaR by chemokine receptors, we evaluated CaR surface expression on cells before and after exposure to the chemokines, SDF-1α or MCP-1. The mean fluorescence intensity of CaR expression was 361+/−25 (mean+/−s.e.m.)

units for untreated monocytes and rose to 673+/−59 following MCP-1 stimulation. Monocytic expression of CaR rose to 519+/−48 with SDF-1α a treatment.

In vivo monocyte migration towards calcium. In order to determine whether $Ca^{++}$ was active as a chemoattractant for monocytes in vivo, calcium chloride alone (5.0 mM), MCP-1 alone, or both $Ca^{++}$ and MCP-1 were injected subcutaneously into C57BL/6 mice, and the tissue was excised 18 hours later. Accumulation of mononuclear cells staining positive for the monocytic marker, Mac-1, was noted in mice injected with either $Ca^{++}$ or MCP-1 or 10 μM NPS R-467. No subcutaneous infiltrates of cells were detected in mice injected with PBS alone. The greatest degree of monocyte infiltration into subcutaneous tissues was seen with 5 mM $Ca^{++}$ plus MCP-1, supporting in vivo the synergistic relationship observed in vitro. No significant infiltrate of neutrophils into the site of subcutaneous injection was seen under any of the conditions used as determined by hematoxylin and eosin staining of skin sections.

Discussion

Ionic calcium is highly regulated in vivo, yet can be elevated in specific tissue microenvironments such as the bone marrow and is particularly altered in the context of ongoing cell death and inflammation. Hypothesizing that this phenomenon may serve as a primitive regulator of immune cells, we examined a number of hematopoietic cell types for expression of the calcium sensing receptor. While this receptor is expressed on primitive hematopoietic cells, it is abundant on mature monocytic cells and, therefore, a candidate mediator of immunologic function of this member of the innate immune system.

Localization of monocyte/macrophages at sites of injury or inflammation is crucial for initiation of their role in host defense and has been demonstrated to be regulated by a number of members of the chemokine family. The calcium sensing receptor is a 7-membrane spanning, G-protein coupled receptor that has been shown to have a number of effects on cell physiology including alteration in differentiation, proliferation and apoptosis [for review, see Brown, E. M., et al., *Vitamins and Hormones*, 1999, 55:1-71]. Whether this molecule alters the motility of primary cells or cells of the immune system had not previously been addressed. We documented the responsiveness of monocytes to signaling through the CaR in a Gαi-coupled and tyrosine kinase, but not PI-3 kinase mediated pathway. The activation of this receptor by either polycationic cognate ligands (e.g. high $Ca^{2+}$ or spermine) or an allosteric activator of the CaR, NPS R-467, resulted in the transmigration of monocytic cells. The absence of chemotaxis of CaR−/− monocytes to Ca++ while responding to a control chemokine defines the specificity of the phenomenon for the CaR. Conjecturing that the Ca++ signal was likely to interact with other mediators of cell response, we assessed whether the migratory response to MCP-1 was similarly modulated by CaR activation. The impact of CaR signaling was manifest in upregulation of MCP-1 receptor as mediated by a mechanism of altered intracellular trafficking rather than new protein synthesis. A reciprocal increase in CaR expression was noted with stimulation of CCR-2 with MCP-1 documenting a clear interrelationship of these two unrelated members of the 7-TM receptor family. This interaction was evident in vivo as well as in vitro when ligands were used in isolation or in combination in animals and generated marked monocytic infiltrates at the site of injection. Thus, ionic calcium serves to directly and indirectly influence monocyte migratory response. It can play a role in the tissue localization of primary monocytes and may potentiate protein-mediated induction of chemotaxis. The contribution of this signal to inflammation is dependent upon local calcium concentrations and therefore may be relevant for settings of either extensive injury or in the context of chronic inflammation.

The CaR induction of monocyte infiltration provides insight regarding the persistence of inflammation at sites of prior injury subsequent to resolution of the inciting event. The presence of local calcium may further monocytic recruitment, thereby perpetuating inflammatory infiltration. Sites of local accumulation of calcium such as atherosclerotic plaques, granulomata, calcific tendonitis or calcium pyrophosphate disease (pseudogout) may provide a reservoir of calcium ions serving to encourage monocyte localization. Interruption of this chemokinetic stimulus through specific inhibition of the CaR therefore provides a therapeutic opportunity in these disease contexts.

Example 2

Calcium ions effect Hematopoietic Progenitor Cells. We also assessed the effects of calcium, through its interaction with the calcium sensing receptor (CaR) using in vitro assays of human $CD34^+$ cells. These demonstrated that an increased $Ca^{2+}$ concentration led to a decrease in the number of more mature BFU-Es (p=0.017), but an increase in the level of primitive cells measured by LTC-ICs (p=0.037). These effects were demonstrated to be CaR receptor-specific through specific CaR agonists and antagonists. Therefore, calcium participates in maintaining candidate stem cells in a primitive, undifferentiated state. Furthermore, migratory properties of primitive hematopoietic cells were altered via CaR as demonstrated by attenuated chemotactic responses to SDF-1α in the setting of CaR activation. In vivo studies using mice engineered to be deficient in the CaR demonstrated a hypocellular bone marrow in comparison to +/+ or +/− littermates. This was accompanied by a decrease in the level of LTC-ICs in the bone marrow, but an increase in the level of CFU-Cs, with a converse increase in hematopoietic stem cells in is the peripheral blood. Further, transplantation of fetal liver cells from CaR−/− mice into wild-type animals demonstrated defective homing and engraftment of CaR−/− stem cells to bone marrow. These data demonstrate that CaR is critical for the maintenance of stem cells in the bone marrow space. Taken together, these data define the CaR as a key regulator of stem cell preservation and bone marrow localization.

DETAILED DESCRIPTION OF THE DRAWINGS

FIG. 1a: $CD14^+$ monocytes stain positively for the CaR, and binding of anti-CaR antibody is inhibitable by preincubation with CaR peptide. Purified peripheral blood CD14+ monocytes (scattergram) were exposed to anti-CaR antibody (solid area in histogram) or isotype control (open area) and examined by flow cytometry. Monocytes were also preincubated with CaR peptide prior to staining with anti-CaR antibody (dashed area). Data represent one of ten independent experiments with comparable results.

Figure 1B:
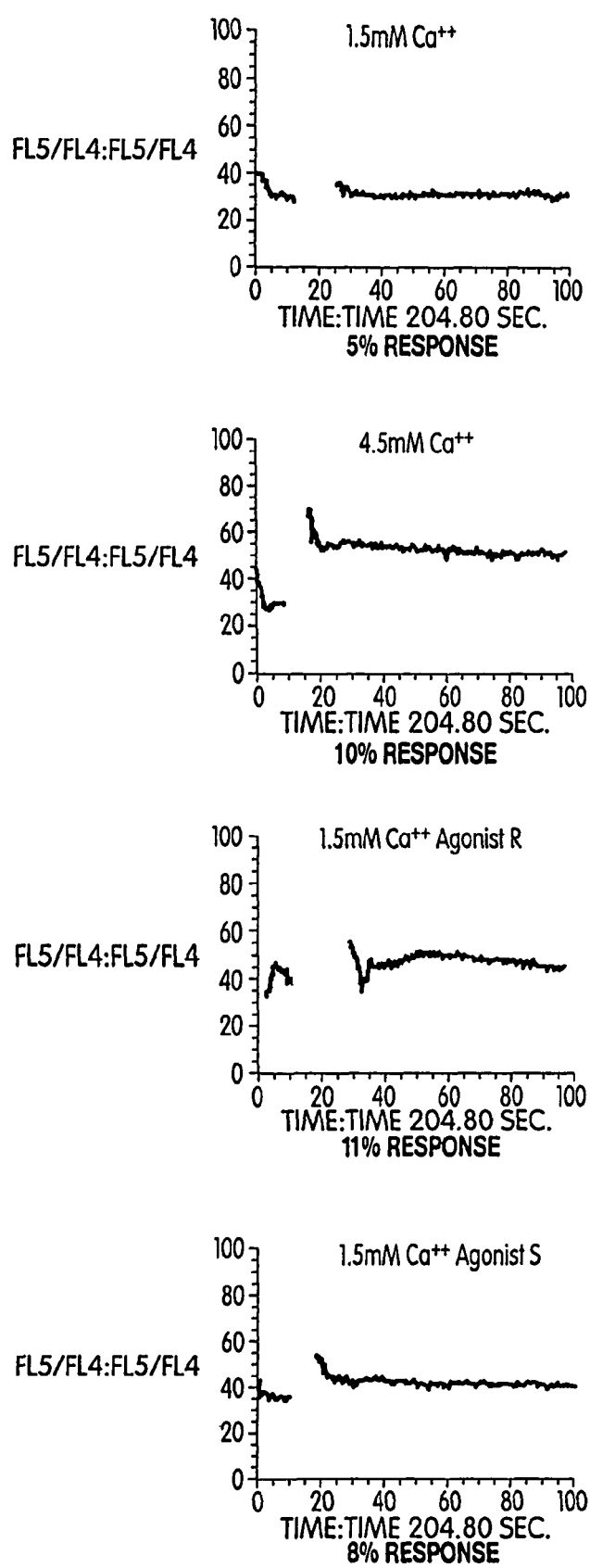
FIG. 1(b) Graphs showing elevation of CD14$^+$ intracellular Ca$^{++}$ concentration following elevation in the extracellular Ca$^{++}$ concentration or addition of the selective CaR activator NPS R-467 in the extracellular medium.

FIG. 1b: Elevating the extracellular $Ca^{++}$ concentration or addition of the selective CaR activator, NPS R-467, induces elevation in cytosolic $Ca^{++}$. Sustained increases in cytosolic calcium were seen in response to 4.5 mM $Ca^{++}$ or 1 μM NPS R-467 or S-467 in the presence of 1.5 mM $Ca^{++}$. All calcium concentrations shown represent the total calcium content of the basal medium plus added calcium. Data are from one of three independent experiments with similar results.

FIG. 2: Monocytes migrate toward $Ca^{++}$ in a dose dependent manner that is inhibitable by pretreatment with PTX, genistein or herbimycin and is potentiated by the selective CaR activator, NPS R-467, and the chemokine, MCP-1. Transmigration assays were used to determine if $Ca^{++}$ was capable of inducing monocyte chemotaxis within a checkerboard analysis (FIG. 2a—upper panel). An input of $1 \times 10^4$ monocytes was utilized and the mean number of cells migrating in response to each $Ca^{++}$ gradient are shown. The results of three independent experiments are shown. A dose dependent effect was seen with maximal chemotaxis observed at 4.5 mM $Ca^{++}$, which was inhibitable by PTX (FIG. 2a—lower panel). Chemotaxis of monocytes towards a positive gradient of $Ca^{++}$ at 3 mM was also inhibitable by pretreatment with the tyrosine kinase inhibitors, genistein (gen) or herbimycin (herb), but not by the PI-3 kinase inhibitor, wortmannin (wort) (FIG. 2b). The role of the CaR in mediating the chemotactic response to elevated $Ca^{++}$ was supported by the greater potency of R-467 than of S-467 in stimulating chemotaxis (FIG. 2c). It should be noted that no specific antagonists or neutralizing antibody for the CaR have been defined to date. *P values represent Student t-Test compared with 3 mM $Ca^{++}$ control. Chemotaxis of peripheral blood monocytes obtained from CaR −/− and CaR+/+ mice was also determined in response to 4.5 mM Ca++ and to MCP-1 in the presence of 1.5 mM Ca++ (FIG. 2d). The percent migration of CaR +/+ monocytes (solid bars) and CaR−/− monocytes (striped bars) are shown. The data from two separate experiments is shown +/−s.e.m. Chemotaxis of $CD14^+$ monocytes to a positive concentration gradient of MCP-1 was also dependent upon and potentiated by $Ca^{++}$. Migration of monocytes in the presence of varying levels of $Ca^{++}$ with MCP-1 (solid columns) or without MCP-1 (hatched columns) are shown. The percentage of cells migrating in response to MCP-1 could be augmented by increased $Ca^{++}$ concentrations with peak additive activity at 4.5 mM $Ca^{++}$ (FIG. 2e). Data represents the mean+/−s.e.m. of at least three independent experiments.

Table 1: Exposure of $CD14^+$ monocytes to $Ca^{++}$ enhances CCR2 expression in a dose dependent manner. Monocytes were exposed to varying concentrations of $Ca^{++}$ and to the selective CaR activator, NPS R-467 (1 μM), or to NPS S-467 (1 μM) in the presence of 1.5 mM $Ca^{++}$. The median fluorescence intensity for CCR2 expression was measured for each $Ca^{++}$ concentration and in the presence of NPS R-467 or S-467. Mean values +/−s.e.m. from three independent experiments are shown.

TABLE 1

| | Mean fluorescent intensity -CCR-2 Mean +/− s.e.m. | p value |
|---|---|---|
| 0 mM $Ca^{++}$ | 204 +/− 16 | — |
| 1.5 mM $Ca^{++}$ | 278 +/− 39 | 0.0045* |
| 2.5 mM $Ca^{++}$ | 296 +/− 35 | 0.0007* |
| 4.5 mM $Ca^{++}$ | 307 +/− 35 | 0.0003* |
| 1.5 mM $Ca^{++}$ and Agonist R | 460 +/− 52 | 0.0135** |
| 1.5 mM $Ca^{++}$ and Agonist S | 417 +/− 48 | 0.0205** |

*t-Test vs 0 mM $Ca^{++}$
**t-Test vs 1.5 mM $Ca^{++}$

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety. What is claimed is presented below and is followed by a Sequence Listing.

We claim:

1. A method for enhancing bone marrow engraftment following bone marrow transplantation, comprising: contacting isolated bone marrow cells to be transplanted with a CaR receptor agonist in an amount effective to increase chemokine receptor expression in the isolated bone marrow cells to enhance bone marrow engraftment following bone marrow transplantation of said cells, wherein the CaR receptor agonist is NPS R-467, thereby enhancing bone marrow engraftment following bone marrow transplantation of said cells.

2. The method of claim 1, wherein the isolated bone marrow cells are hematopoietic progenitor cells.

3. The method of claim 1, wherein the chemokine receptor is the selected from the group consisting of CCR-2, CCR-5, and CXCR-4.

4. A method for increasing bone marrow engraftment following bone marrow transplantation, comprising: contacting isolated bone marrow cells to be transplanted with NPS R-467 in an effective amount to increase chemokine receptor expression in the isolated bone marrow cells to increase bone marrow engraftment following bone marrow transplantation of said cells.

5. The method of claim 4, wherein the cells are also contacted with calcium.

6. A method for increasing bone marrow engraftment following bone marrow transplantation, comprising: contacting isolated bone marrow cells to be transplanted with Vitamin D in an effective amount to increase CaR receptor expression in the isolated bone marrow cells to enhance bone marrow engraftment following bone marrow transplantation of said cells.

7. A method for enhancing engraftment of isolated bone marrow cells in bone marrow following bone marrow transplantation, comprising:

contacting the isolated bone marrow cells to be transplanted with a non-$Ca^{++}$ CaR receptor agonist in an amount effective to increase chemokine receptor expression in the isolated bone marrow cells to enhance engraftment of the isolated bone marrow cells in the bone marrow following bone marrow transplantation of said cells, wherein the CaR receptor agonist is NPS R-467, thereby enhancing engraftment of the isolated bone marrow cells in the bone marrow following bone marrow transplantation of said cells.

8. A method for enhancing engraftment of isolated bone marrow cells in bone marrow following bone marrow transplantation, comprising:

contacting the isolated bone marrow cells to be transplanted with an agent that increases CaR receptor expression in an amount effective to increase CaR receptor expression in the isolated bone marrow cells to enhance engraftment of the isolated bone marrow cells in the bone marrow following bone marrow transplantation of said cells, wherein the agent that increases CaR receptor expression is Vitamin D, thereby enhancing engraftment of the isolated bone marrow cells in the bone marrow following bone marrow transplantation of said cells.

9. A method for enhancing engraftment of isolated bone marrow cells in bone marrow following bone marrow transplantation, comprising:

contacting the isolated bone marrow cells to be transplanted with an agent that increases CaR receptor expression in an amount effective to increase CaR receptor expression in the isolated bone marrow cells to enhance engraftment of the isolated bone marrow cells in the bone marrow following bone marrow transplantation of said cells, wherein the agent is IL-1-$\beta$, thereby enhancing engraftment of the isolated bone marrow cells in the bone marrow following bone marrow transplantation of said cells.

10. The method of claim 9, wherein the isolated bone marrow cells are hematopoietic progenitor cells.

* * * * *

SEQUENCE LISTING

<160> NUMBER OF SEQ ID NOS: 2

<210> SEQ ID NO 1
<211> LENGTH: 3361
<212> TYPE: DNA
<213> ORGANISM: Homo sapiens
<220> FEATURE:
<221> NAME/KEY: CDS
<222> LOCATION: (29)..(3262)

<400> SEQUENCE: 1

```
tcccttgccc tggagagacg gcagaacc atg gca ttt tat agc tgc tgc tgg      52
                             Met Ala Phe Tyr Ser Cys Cys Trp
                               1               5 gtc ctc ttg gca ctc acc tgg cac acc tct gcc tac ggg cca gac cag    100
Val Leu Leu Ala Leu Thr Trp His Thr Ser Ala Tyr Gly Pro Asp Gln
         10                  15                  20 cga gcc caa aag aag ggg gac att atc ctt ggg ggg ctc ttt cct att    148
Arg Ala Gln Lys Lys Gly Asp Ile Ile Leu Gly Gly Leu Phe Pro Ile
 25                  30                  35                  40 cat ttt gga gta gca gct aaa gat caa gat ctc aaa tca agg ccg gag    196
His Phe Gly Val Ala Ala Lys Asp Gln Asp Leu Lys Ser Arg Pro Glu
                 45                  50                  55 tct gtg gaa tgt atc agg tat aat ttc cgt ggg ttt cgc tgg tta cag    244
Ser Val Glu Cys Ile Arg Tyr Asn Phe Arg Gly Phe Arg Trp Leu Gln
             60                  65                  70
```

-continued

| | |
|---|---|
| gct atg ata ttt gcc ata gag gag ata aac agc agc cca gcc ctt ctt<br>Ala Met Ile Phe Ala Ile Glu Glu Ile Asn Ser Ser Pro Ala Leu Leu<br>75                  80                  85 | 292 |
| ccc aac ttg acg ctg gga tac agg ata ttt gac act tgc aac acc gtt<br>Pro Asn Leu Thr Leu Gly Tyr Arg Ile Phe Asp Thr Cys Asn Thr Val<br>    90                  95                  100 | 340 |
| tct aag gcc ttg gaa gcc acc ctg agt ttt gtt gct caa aac aaa att<br>Ser Lys Ala Leu Glu Ala Thr Leu Ser Phe Val Ala Gln Asn Lys Ile<br>105                 110                 115                 120 | 388 |
| gat tct ttg aac ctt gat gag ttc tgc aac tgc tca gag cac att ccc<br>Asp Ser Leu Asn Leu Asp Glu Phe Cys Asn Cys Ser Glu His Ile Pro<br>                125                 130                 135 | 436 |
| tct acg att gct gtg gtg gga gca act ggc tca ggc gtc tcc acg gca<br>Ser Thr Ile Ala Val Val Gly Ala Thr Gly Ser Gly Val Ser Thr Ala<br>            140                 145                 150 | 484 |
| gtg gca aat ctg ctg ggg ctc ttc tac att ccc cag gtc agt tat gcc<br>Val Ala Asn Leu Leu Gly Leu Phe Tyr Ile Pro Gln Val Ser Tyr Ala<br>        155                 160                 165 | 532 |
| tcc tcc agc aga ctc ctc agc aac aag aat caa ttc aag tct ttc ctc<br>Ser Ser Ser Arg Leu Leu Ser Asn Lys Asn Gln Phe Lys Ser Phe Leu<br>    170                 175                 180 | 580 |
| cga acc atc ccc aat gat gag cac cag gcc act gcc atg gca gac atc<br>Arg Thr Ile Pro Asn Asp Glu His Gln Ala Thr Ala Met Ala Asp Ile<br>185                 190                 195                 200 | 628 |
| atc gag tat ttc cgc tgg aac tgg gtg ggc aca att gca gct gat gac<br>Ile Glu Tyr Phe Arg Trp Asn Trp Val Gly Thr Ile Ala Ala Asp Asp<br>                205                 210                 215 | 676 |
| gac tat ggg cgg ccg ggg att gag aaa ttc cga gag gaa gct gag gaa<br>Asp Tyr Gly Arg Pro Gly Ile Glu Lys Phe Arg Glu Glu Ala Glu Glu<br>            220                 225                 230 | 724 |
| agg gat atc tgc atc gac ttc agt gaa ctc atc tcc cag tac tct gat<br>Arg Asp Ile Cys Ile Asp Phe Ser Glu Leu Ile Ser Gln Tyr Ser Asp<br>        235                 240                 245 | 772 |
| gag gaa gag atc cag cat gtg gta gag gtg att caa aat tcc acg gcc<br>Glu Glu Glu Ile Gln His Val Val Glu Val Ile Gln Asn Ser Thr Ala<br>    250                 255                 260 | 820 |
| aaa gtc atc gtg gtt ttc tcc agt ggc cca gat ctt gag ccc ctc atc<br>Lys Val Ile Val Val Phe Ser Ser Gly Pro Asp Leu Glu Pro Leu Ile<br>265                 270                 275                 280 | 868 |
| aag gag att gtc cgg cgc aat atc acg ggc aag atc tgg ctg gcc agc<br>Lys Glu Ile Val Arg Arg Asn Ile Thr Gly Lys Ile Trp Leu Ala Ser<br>                285                 290                 295 | 916 |
| gag gcc tgg gcc agc tcc tcc ctg atc gcc atg cct cag tac ttc cac<br>Glu Ala Trp Ala Ser Ser Ser Leu Ile Ala Met Pro Gln Tyr Phe His<br>            300                 305                 310 | 964 |
| gtg gtt ggc ggc acc att gga ttc gct ctg aag gct ggg cag atc cca<br>Val Val Gly Gly Thr Ile Gly Phe Ala Leu Lys Ala Gly Gln Ile Pro<br>        315                 320                 325 | 1012 |
| ggc ttc cgg gaa ttc ctg aag aag gtc cat ccc agg aag tct gtc cac<br>Gly Phe Arg Glu Phe Leu Lys Lys Val His Pro Arg Lys Ser Val His<br>    330                 335                 340 | 1060 |
| aat ggt ttt gcc aag gag ttt tgg gaa gaa aca ttt aac tgc cac ctc<br>Asn Gly Phe Ala Lys Glu Phe Trp Glu Glu Thr Phe Asn Cys His Leu<br>345                 350                 355                 360 | 1108 |
| caa gaa ggt gca aaa gga cct tta cct gtg gac acc ttt ctg aga ggt<br>Gln Glu Gly Ala Lys Gly Pro Leu Pro Val Asp Thr Phe Leu Arg Gly<br>                365                 370                 375 | 1156 |
| cac gaa gaa agt ggc gac agg ttt agc aac agc tcg aca gcc ttc cga<br>His Glu Glu Ser Gly Asp Arg Phe Ser Asn Ser Ser Thr Ala Phe Arg<br>            380                 385                 390 | 1204 |

```
ccc ctc tgt aca ggg gat gag aac atc agc agt gtc gag acc cct tac          1252
Pro Leu Cys Thr Gly Asp Glu Asn Ile Ser Ser Val Glu Thr Pro Tyr
        395             400             405 ata gat tac acg cat tta cgg ata tcc tac aat gtg tac tta gca gtc          1300
Ile Asp Tyr Thr His Leu Arg Ile Ser Tyr Asn Val Tyr Leu Ala Val
410             415             420 tac tcc att gcc cac gcc ttg caa gat ata tat acc tgc tta cct ggg          1348
Tyr Ser Ile Ala His Ala Leu Gln Asp Ile Tyr Thr Cys Leu Pro Gly
425             430             435             440 aga ggg ctc ttc acc aat ggc tcc tgt gca gac atc aag aaa gtt gag          1396
Arg Gly Leu Phe Thr Asn Gly Ser Cys Ala Asp Ile Lys Lys Val Glu
                445             450             455 gcg tgg cag gtc ctg aag cac cta cgg cat cta aac ttt aca aac aat          1444
Ala Trp Gln Val Leu Lys His Leu Arg His Leu Asn Phe Thr Asn Asn
            460             465             470 atg ggg gag cag gtg acc ttt gat gag tgt ggt gac ctg gtg ggg aac          1492
Met Gly Glu Gln Val Thr Phe Asp Glu Cys Gly Asp Leu Val Gly Asn
        475             480             485 tat tcc atc atc aac tgg cac ctc tcc cca gag gat ggc tcc atc gtg          1540
Tyr Ser Ile Ile Asn Trp His Leu Ser Pro Glu Asp Gly Ser Ile Val
490             495             500 ttt aag gaa gtc ggg tat tac aac gtc tat gcc aag aag gga gaa aga          1588
Phe Lys Glu Val Gly Tyr Tyr Asn Val Tyr Ala Lys Lys Gly Glu Arg
505             510             515             520 ctc ttc atc aac gag gag aaa atc ctg tgg agt ggg ttc tcc agg gag          1636
Leu Phe Ile Asn Glu Glu Lys Ile Leu Trp Ser Gly Phe Ser Arg Glu
                525             530             535 gtg ccc ttc tcc aac tgc agc cga gac tgc ctg gca ggg acc agg aaa          1684
Val Pro Phe Ser Asn Cys Ser Arg Asp Cys Leu Ala Gly Thr Arg Lys
            540             545             550 ggg atc att gag ggg gag ccc acc tgc tgc ttt gag tgt gtg gag tgt          1732
Gly Ile Ile Glu Gly Glu Pro Thr Cys Cys Phe Glu Cys Val Glu Cys
        555             560             565 cct gat ggg gag tat agt gat gag aca gat gcc agt gcc tgt aac aag          1780
Pro Asp Gly Glu Tyr Ser Asp Glu Thr Asp Ala Ser Ala Cys Asn Lys
570             575             580 tgc cca gat gac ttc tgg tcc aat gag aac cac acc tcc tgc att gcc          1828
Cys Pro Asp Asp Phe Trp Ser Asn Glu Asn His Thr Ser Cys Ile Ala
585             590             595             600 aag gag atc gag ttt ctg tcg tgg acg gag ccc ttt ggg atc gca ctc          1876
Lys Glu Ile Glu Phe Leu Ser Trp Thr Glu Pro Phe Gly Ile Ala Leu
                605             610             615 acc ctc ttt gcc gtg ctg ggc att ttc ctg aca gcc ttt gtg ctg ggt          1924
Thr Leu Phe Ala Val Leu Gly Ile Phe Leu Thr Ala Phe Val Leu Gly
            620             625             630 gtg ttt atc aag ttc cgc aac aca ccc att gtc aag gcc acc aac cga          1972
Val Phe Ile Lys Phe Arg Asn Thr Pro Ile Val Lys Ala Thr Asn Arg
        635             640             645 gag ctc tcc tac ctc ctc ctc ttc tcc ctg ctc tgc tgc ttc tcc agc          2020
Glu Leu Ser Tyr Leu Leu Leu Phe Ser Leu Leu Cys Cys Phe Ser Ser
650             655             660 tcc ctg ttc ttc atc ggg gag ccc cag gac tgg acg tgc cgc ctg cgc          2068
Ser Leu Phe Phe Ile Gly Glu Pro Gln Asp Trp Thr Cys Arg Leu Arg
665             670             675             680 cag ccg gcc ttt ggc atc agc ttc gtc ctc tgc atc tca tgc atc ctg          2116
Gln Pro Ala Phe Gly Ile Ser Phe Val Leu Cys Ile Ser Cys Ile Leu
                685             690             695 gtg aaa acc aac cgt gtc ctc ctg gtg ttt gag gcc aag atc ccc acc          2164
Val Lys Thr Asn Arg Val Leu Leu Val Phe Glu Ala Lys Ile Pro Thr
            700             705             710
```

-continued

| | | |
|---|---|---|
| agc ttc cac cgc aag tgg tgg ggg ctc aac ctg cag ttc ctg ctg gtt<br>Ser Phe His Arg Lys Trp Trp Gly Leu Asn Leu Gln Phe Leu Leu Val<br>715                  720                725 | 2212 |
| ttc ctc tgc acc ttc atg cag att gtc atc tgt gtg atc tgg ctc tac<br>Phe Leu Cys Thr Phe Met Gln Ile Val Ile Cys Val Ile Trp Leu Tyr<br>730                  735                740 | 2260 |
| acc gcg ccc ccc tca agc tac cgc aac cag gag ctg gag gat gag atc<br>Thr Ala Pro Pro Ser Ser Tyr Arg Asn Gln Glu Leu Glu Asp Glu Ile<br>745                  750              755              760 | 2308 |
| atc ttc atc acg tgc cac gag ggc tcc ctc atg gcc ctg ggc ttc ctg<br>Ile Phe Ile Thr Cys His Glu Gly Ser Leu Met Ala Leu Gly Phe Leu<br>                765              770              775 | 2356 |
| atc ggc tac acc tgc ctg ctg gct gcc atc tgc ttc ttt gcc ttc<br>Ile Gly Tyr Thr Cys Leu Leu Ala Ala Ile Cys Phe Phe Ala Phe<br>                780              785              790 | 2404 |
| aag tcc cgg aag ctg ccg gag aac ttc aat gaa gcc aag ttc atc acc<br>Lys Ser Arg Lys Leu Pro Glu Asn Phe Asn Glu Ala Lys Phe Ile Thr<br>         795               800              805 | 2452 |
| ttc agc atg ctc atc ttc ttc atc gtc tgg atc tcc ttc att cca gcc<br>Phe Ser Met Leu Ile Phe Phe Ile Val Trp Ile Ser Phe Ile Pro Ala<br>810                  815                820 | 2500 |
| tat gcc agc acc tat ggc aag ttt gtc tct gcc gta gag gtg att gcc<br>Tyr Ala Ser Thr Tyr Gly Lys Phe Val Ser Ala Val Glu Val Ile Ala<br>825                  830              835              840 | 2548 |
| atc ctg gca gcc agc ttt ggg ttg ctg gcg tgc atc ttc ttc aac aag<br>Ile Leu Ala Ala Ser Phe Gly Leu Leu Ala Cys Ile Phe Phe Asn Lys<br>                845              850              855 | 2596 |
| acc tac atc att ctc ttc aag cca tcc cgc aac acc atc gag gag gtg<br>Thr Tyr Ile Ile Leu Phe Lys Pro Ser Arg Asn Thr Ile Glu Glu Val<br>                  860              865              870 | 2644 |
| cgt tgc agc acc gca cgt cac gct ttc aag gtg gct gcc cgg gcc acg<br>Arg Cys Ser Thr Ala Arg His Ala Phe Lys Val Ala Ala Arg Ala Thr<br>875                  880              885 | 2692 |
| ctg cgc cgc agc aac gtc tcc cgc aag cgg tcc agc agc ctt gga ggc<br>Leu Arg Arg Ser Asn Val Ser Arg Lys Arg Ser Ser Ser Leu Gly Gly<br>890                  895              900 | 2740 |
| tcc acg gga tcc acc ccc tcc tcc tcc atc agc agc aag agc aac agc<br>Ser Thr Gly Ser Thr Pro Ser Ser Ser Ile Ser Ser Lys Ser Asn Ser<br>905                  910              915              920 | 2788 |
| gaa gac cca ttc cca cag ccc gag agg cag aag cag cag ccg ctg<br>Glu Asp Pro Phe Pro Gln Pro Glu Arg Gln Lys Gln Gln Gln Pro Leu<br>                925              930              935 | 2836 |
| gcc cta acc cag caa gag cag cag cag cag ccc ctg acc ctc cca cag<br>Ala Leu Thr Gln Gln Glu Gln Gln Gln Gln Pro Leu Thr Leu Pro Gln<br>940                  945              950 | 2884 |
| cag caa cga tct cag cag cag ccc aga tgc aag cag aag gtc atc ttt<br>Gln Gln Arg Ser Gln Gln Gln Pro Arg Cys Lys Gln Lys Val Ile Phe<br>         955               960              965 | 2932 |
| ggc agc ggc acg gtc acc ttc tca ctg agc ttt gat gag cct cag aag<br>Gly Ser Gly Thr Val Thr Phe Ser Leu Ser Phe Asp Glu Pro Gln Lys<br>                970              975              980 | 2980 |
| aac gcc atg gcc cac agg aat tct acg cac cag aac tcc ctg gag gcc<br>Asn Ala Met Ala His Arg Asn Ser Thr His Gln Asn Ser Leu Glu Ala<br>985                  990              995           1000 | 3028 |
| cag aaa agc agc gat acg ctg acc cga cac cag cca tta ctc ccg ctg<br>Gln Lys Ser Ser Asp Thr Leu Thr Arg His Gln Pro Leu Leu Pro Leu<br>                1005              1010            1015 | 3076 |
| cag tgc ggg gaa acg gac tta gat ctg acc gtc cag gaa aca ggt ctg<br>Gln Cys Gly Glu Thr Asp Leu Asp Leu Thr Val Gln Glu Thr Gly Leu<br>1020                  1025              1030 | 3124 |

```
caa gga cct gtg ggt gga gac cag cgg cca gag gtg gag gac cct gaa    3172
Gln Gly Pro Val Gly Gly Asp Gln Arg Pro Glu Val Glu Asp Pro Glu
        1035                1040                1045 gag ttg tcc cca gca ctt gta gtg tcc agt tca cag agc ttt gtc atc    3220
Glu Leu Ser Pro Ala Leu Val Val Ser Ser Gln Ser Phe Val Ile
    1050                1055                1060 agt ggt gga ggc agc act gtt aca gaa aac gta gtg aat tca            3262
Ser Gly Gly Gly Ser Thr Val Thr Glu Asn Val Val Asn Ser
1065            1070                1075 taaaatggaa ggagaagact gggctaggga gaatgcagag aggtttcttg ggtcccagg   3322 gatgaggaat cgccccagac tcctttcctc tgaggaaga                         3361

<210> SEQ ID NO 2
<211> LENGTH: 1078
<212> TYPE: PRT
<213> ORGANISM: Homo sapiens

<400> SEQUENCE: 2

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300
```

-continued

```
Ile Ala Met Pro Gln Tyr Phe His Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
```

-continued

```
              725                 730                 735
Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
        755                 760                 765

Ser Leu Met Ala Leu Gly Phe Leu Ile Gly Tyr Thr Cys Leu Leu Ala
        770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
                820                 825                 830

Val Ser Ala Val Glu Val Ile Ala Ile Leu Ala Ala Ser Phe Gly Leu
            835                 840                 845

Leu Ala Cys Ile Phe Phe Asn Lys Thr Tyr Ile Ile Leu Phe Lys Pro
        850                 855                 860

Ser Arg Asn Thr Ile Glu Glu Val Arg Cys Ser Thr Ala Arg His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Gln Pro Leu Ala Leu Thr Gln Gln Glu Gln Gln
    930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala Gln Lys Ser Ser Asp Thr Leu Thr
        995                1000                1005

Arg His Gln Pro Leu Leu Pro Leu Gln Cys Gly Glu Thr Asp Leu Asp
    1010                1015                1020

Leu Thr Val Gln Glu Thr Gly Leu Gln Gly Pro Val Gly Gly Asp Gln
1025                1030                1035                1040

Arg Pro Glu Val Glu Asp Pro Glu Glu Leu Ser Pro Ala Leu Val Val
                1045                1050                1055

Ser Ser Ser Gln Ser Phe Val Ile Ser Gly Gly Gly Ser Thr Val Thr
            1060                1065                1070

Glu Asn Val Val Asn Ser
        1075
```